(12) United States Patent
Marshall et al.

(10) Patent No.: US 8,199,988 B2
(45) Date of Patent: Jun. 12, 2012

(54) METHOD AND APPARATUS FOR COMBINING 3D DENTAL SCANS WITH OTHER 3D DATA SETS

(75) Inventors: Michael Craig Marshall, Prior Lake, MN (US); Bruce Willard Hultgren, Victoria, MN (US)

(73) Assignee: Geodigm Corporation, Falcon Heights, MN (US)

( * ) Notice: Subject to any disclaimer, the term of this patent is extended or adjusted under 35 U.S.C. 154(b) by 423 days.

(21) Appl. No.: 12/454,368

(22) Filed: May 15, 2009

(65) Prior Publication Data

US 2009/0316966 A1    Dec. 24, 2009

Related U.S. Application Data

(60) Provisional application No. 61/131,902, filed on May 16, 2008, provisional application No. 61/205,191, filed on Jan. 20, 2009.

(51) Int. Cl.
*G06K 9/00* (2006.01)
(52) U.S. Cl. .................. 382/128; 382/100; 709/203
(58) Field of Classification Search .................. 382/128, 382/100; 709/203
See application file for complete search history.

(56) References Cited

U.S. PATENT DOCUMENTS

| | | | |
|---|---|---|---|
| 4,575,805 A | 3/1986 | Moermann et al. | |
| 4,611,288 A | 9/1986 | Duret et al. | |
| 4,837,732 A | 6/1989 | Brandestini et al. | |
| 5,113,424 A | 5/1992 | Burdea et al. | |
| 5,267,293 A | 11/1993 | Virta | |
| 5,273,429 A | 12/1993 | Rekow et al. | |
| 5,343,391 A | 8/1994 | Mushabac | |
| 5,347,454 A | 9/1994 | Mushabac | |
| 5,368,478 A | 11/1994 | Andreiko et al. | |
| 5,372,502 A | 12/1994 | Massen et al. | |
| 5,416,822 A | 5/1995 | Kunik | |
| 5,431,562 A | 7/1995 | Andreiko et al. | |
| 5,448,472 A | 9/1995 | Mushabac | |
| 5,518,397 A | 5/1996 | Andreiko et al. | |
| 5,533,895 A | 7/1996 | Andreiko et al. | |
| 5,549,476 A | 8/1996 | Stern | |

(Continued)

FOREIGN PATENT DOCUMENTS

WO    2007/130574    11/2007

OTHER PUBLICATIONS

Search Report Mailed Dec. 23, 2009; International Application No. PCT/US2009/044108.

(Continued)

*Primary Examiner* — Joseph Chang
(74) *Attorney, Agent, or Firm* — Merchant & Gould P.C.

(57) ABSTRACT

By matching a first data set including digital, three-dimensional, dental models with a second data set including digital, cranio-facial 3D medical scan records, missing or inaccurate portions of the cranio-facial 3D medical scan record can be improved. Example methods for matching the data sets include automatically positioning the dental model with respect to the 3D medical scan record and automatically eliminating common (i.e., overlapping) portions from one of the data sets. Two-dimensional images can be mapped onto images generated from either of the first and second data sets to enhance accuracy and/or photo-realism.

20 Claims, 36 Drawing Sheets
(22 of 36 Drawing Sheet(s) Filed in Color)

U.S. PATENT DOCUMENTS

| | | | |
|---|---|---|---|
| 5,569,578 A | 10/1996 | Mushabac | |
| 5,588,430 A | 12/1996 | Bova et al. | |
| 5,605,459 A | 2/1997 | Kuroda et al. | |
| 5,879,158 A | 3/1999 | Doyle et al. | |
| 6,068,482 A | 5/2000 | Snow | |
| 6,123,544 A | 9/2000 | Cleary | |
| 6,143,003 A | 11/2000 | Cosman | |
| 6,322,359 B1 | 11/2001 | Jordan et al. | |
| 6,371,761 B1 | 4/2002 | Cheang et al. | |
| 6,409,504 B1 | 6/2002 | Jones et al. | |
| 6,450,807 B1 | 9/2002 | Chishti et al. | |
| 6,554,613 B1 | 4/2003 | Sachdeva et al. | |
| 6,632,089 B2 | 10/2003 | Rubbert et al. | |
| 6,648,640 B2 | 11/2003 | Rubbert et al. | |
| 6,688,886 B2 | 2/2004 | Hughes et al. | |
| 6,905,337 B1 | 6/2005 | Sachdeva | |
| 7,039,156 B2 | 5/2006 | Arai et al. | |
| 7,092,483 B2 | 8/2006 | Nyholm | |
| 7,387,511 B2 | 6/2008 | Marshall | |
| 7,747,305 B2 * | 6/2010 | Dean et al. | 600/407 |
| 2004/0015327 A1 | 1/2004 | Sachdeva et al. | |
| 2004/0119817 A1 | 6/2004 | Maddison et al. | |
| 2005/0144222 A1 | 6/2005 | Marshall | |
| 2009/0177454 A1 * | 7/2009 | Bronstein et al. | 703/11 |

OTHER PUBLICATIONS

Hayashi, T. et al., "A Computerized System for Analyzing Occlusal Relations During Mandibular Movements," The Intl. Journal of Prosthodontics, vol. 7, No. 2, pp. 108-114 (Mar./Apr. 1994).

* cited by examiner

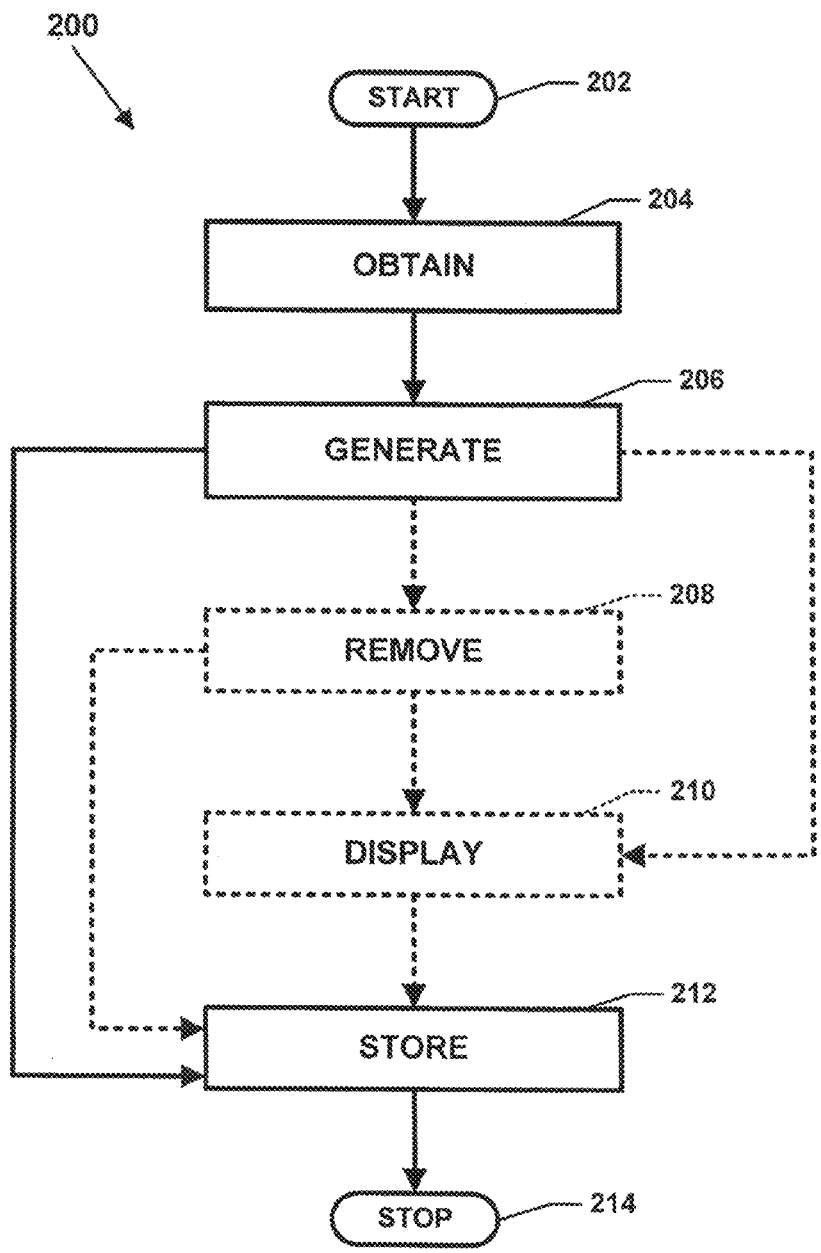

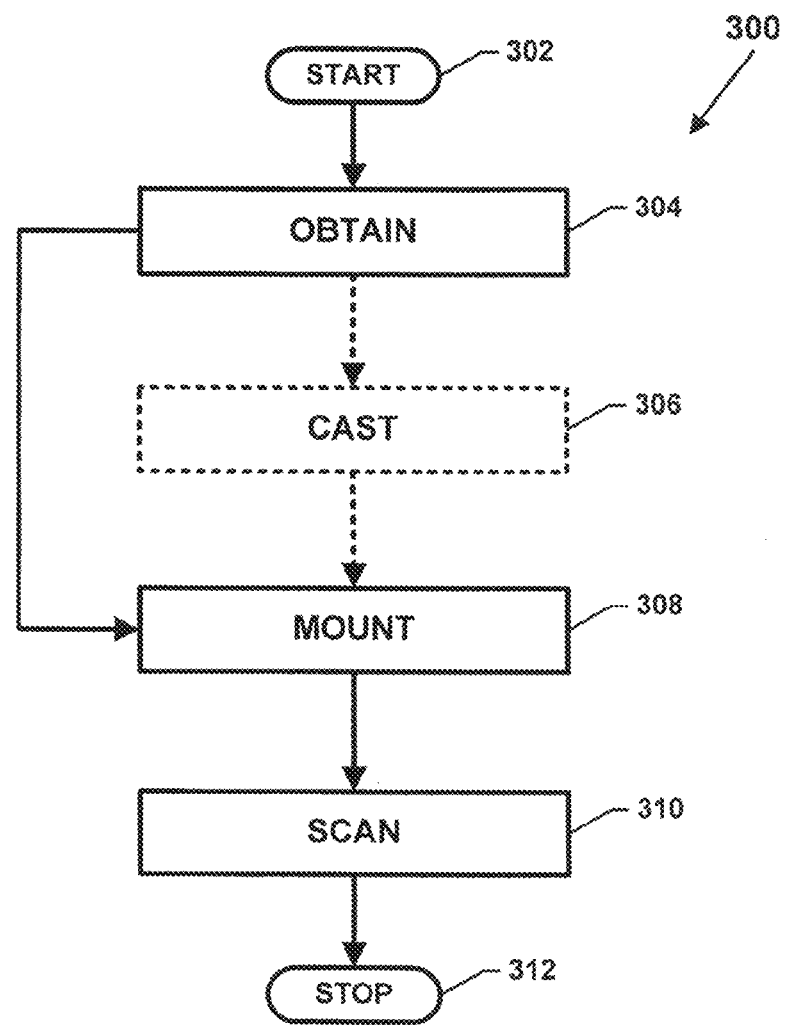

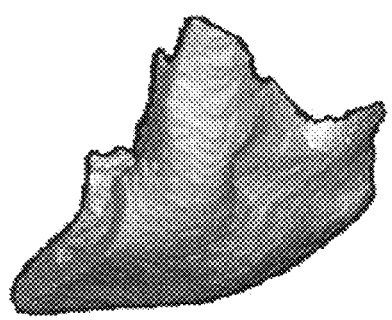
FIG. 24

METHOD AND APPARATUS FOR COMBINING 3D DENTAL SCANS WITH OTHER 3D DATA SETS

CROSS-REFERENCE TO RELATED APPLICATIONS

This application claims the benefit of provisional application Ser. No. 61/131,902, filed May 16, 2008, titled "Method and Apparatus for Combining CT Scans and Dental Scans" and provisional application Ser. No. 61/205,191, filed Jan. 20, 2009, titled "Method and Apparatus for Combining Cone Beam Scans and Dental Scans," both of which are incorporated herein by reference in their entirety.

FIELD

The present disclosure relates generally to dental modeling and imaging; and, more particularly, to positioning digital, three-dimensional, dental models of a patient within digital, three-dimensional data sets (e.g., a cranio-facial cone beam scan record, an MRI scan record, etc.).

BACKGROUND

Patients undergoing oral surgery will typically be prescribed by their doctor to have a medical scan record created of the affected cranio-facial region of the respective patient's skull. Such medical scan records can include computerized axial tomography (CT scan or CAT scan) records, Cone Beam Computed Tomography (CBCT) records, and Magnetic Resonance Imaging (MRI) records. For example, patients undergoing correction of facial deformities, facial reconstruction after injury, and placement of dental implants often will have such a CAT scan, CBCT scan, or MRI scan performed prior to treatment or surgery.

CAT scan records can essentially be described as a series of X-Rays taken a short distance apart along a set path, whereby a three-dimensional presentation of the patient's bone structure, nerves, and facial soft tissue can be generated on a computer screen for aiding the doctor in the determination of the patient's treatment diagnosis. CBCT scanners use a cone shaped x-ray beam to generate a volume of data that can be reconstructed to produce a stack of two-dimensional gray scale level images. Cone beam tomography scanners emit lower radiation than traditional dental x-rays. MRI scanners produce a rotating magnetic field within the body that is detectable by the scanner. For the purposes of this document, the terms CAT scan, CBCT scan, and MRI scan will be referred to collectively as 3D medical scans.

In the application of oral surgery, 3D medical scan records commonly have missing or inaccurate medical information in the region of the teeth occlusal surfaces. Some missing or inaccurate data is caused by the presence of metal dental fillings or metal dental prostheses (crowns, bridges, etc.) in and/or near the patient's teeth. Metal tends to scatter the gamma X-rays generated during the scans, thereby producing a "data void" in the oral region of the scan record in which the metal is present. 3D medical scan accuracy also can be limited by voxel size. In the case of CT scans, imaging accuracy can be limited by the amount of radiation the patient can tolerate in each scanning session. For years, efforts have been made to improve 3D medical scanning accuracy. To date, however, the problem of missing and/or inaccurate medical information in the regions of the occlusal surfaces has not been eliminated.

More accurate electronic data records of teeth occlusal surfaces (hereafter referred to as "dental models") can be generated by scanning the teeth directly, by scanning impressions of the teeth, and/or by scanning models (e.g., casts) of the teeth using a laser-line scanner, optical scanner, or touch scanner. For example, U.S. Pat. No. 6,217,334 (Dental Scanning Method and Apparatus) and U.S. Pat. No. 6,579,095 (Mating Parts Scanning and Registration), each of which are commonly owned by the assignee hereof, disclose systems for creating one or more electronic, three-dimensional, laser-imaged, dental models of patient teeth and surrounding soft tissues (hereafter referred to collectively as "dentition" for convenience). These two identified patents are hereby incorporated herein by reference and made a part hereof.

Efforts to physically locate such dental models into 3D medical scan records have generally required the use of artificial fiducial structures or markers. More specifically, several markers are typically arranged on a dental impression tray, which is held in the patient's mouth during acquisition of the 3D medical scan record. The teeth are then scanned intraorally with the markers arranged in the same position to obtain one or more dental model records. Alternatively, an impression tray or a study cast can be digitized (e.g., through laser scanning, touch-probe scanning, optical scanning, etc.) subsequent to the 3D medical scan to create one or more dental models (e.g., polygonal mesh models) of the teeth. The markers function as fiducial or registration points when combining the dental model record and the 3D medical scan record.

A drawback of these previous efforts, however, is that the 3D medical scan records and the dental models cannot be taken concurrently. Further, it can be beneficial to combine the 3D medical scan records and the dental model records even when the records were not initially taken with the intention to combine the same (e.g., when the records were taken without artificial fiducial structures).

Therefore, there arises a need for a method and apparatus which provides for combining dental model records with 3D medical scans and/or enhances the 3D medical scan medical records of patients considering or undergoing oral surgery.

SUMMARY

The present disclosure provides a method and apparatus for matching a first data set comprising digital, three-dimensional, dental models with a second data set comprising digital, three-dimensional, cranio-facial 3D medical scan records. By combining these data sets, missing or inaccurate portions of the cranio-facial 3D medical scan record can be improved.

The present disclosure provides for automatically determining an appropriate location for one or more electronic, three-dimensional, dental models within a cranio-facial 3D medical scan image. In one embodiment, the dental model includes a first dental model representing a maxillary dental arch or portion thereof and a second dental model representing a mandibular dental arch or portion thereof. In another embodiment, the cranio-facial 3D medical scan record can represent hard and/or soft tissue of the mandible, the maxilla, and/or other portions of the patient's skull.

Initially, the first and second data sets are acquired. Each of the data sets can be taken in its customary manner without requiring the addition of artificial registration markers common between the two images. In certain embodiments, the data sets are acquired at different times and/or locations. In one embodiment, the acquisition of each data set can be performed just prior to the combination of the data sets. In another embodiment, the acquisition of one or both of the data sets can be performed at a previous time in the past. A dental model image and a 3D medical scan image can be generated based on the acquired data.

After acquisition, the 3D medical scan data set is converted to a surface mesh data set, from which a mesh image of the scanned region of the patient can be generated. This conversion can be accomplished by utilizing commercially available algorithms. Optionally, the mandibular and maxillary portions of the surface mesh can be segmented from one another. The dental model data set, after acquisition, is overlaid with the converted surface mesh data set of the 3D medical scan record. In one embodiment, a dental model image is shown superimposed over a 3D medical scan image. This general overlay can be performed using a rough match-up algorithm.

The relative positioning of the first data set (i.e., dental model) and second data set (i.e., 3D medical scan) is then refined by using a matching process. Such a matching process preferably uses a best-fit algorithm, such as an iterative, close point algorithm to move the dental model representing the patient's dentition into closer alignment with the appropriate section of the 3D medical scan record. For example, the matching process can adjust the positioning of maxillary and mandibular dental model images generated from the first data set to align with the maxilla and mandible portions of a 3D medical scan image generated from the second data set.

In order to eliminate the occlusal surface portion of the 3D medical scan record (i.e., to avoid the collision of duplicative data between the 3D medical scan data set and the dental model data set), an elimination volume can be defined within the 3D medical scan record. Any points of the 3D medical scan surface mesh located within the elimination volume can be deleted, thereby eliminating the occlusal surface portion of the 3D medical scan record. In one embodiment, the elimination volume can be defined as the virtual space occupied by the dental model. For example, the elimination volume can be defined as the virtual space occupied by a dental model of a maxillary arch, a dental model of a mandibular arch, and any space located therebetween when the dental models are positioned relative to each other.

According to one aspect of the present disclosure, two different types of three-dimensional data can be combined without fiducials. In one embodiment, a dental record can be combined with a 3D medical scan.

According to another aspect, the dental model provides an accurate data set from which the 3D medical scan data can be recalibrated and adjusted. This recalibration can provide an improved 3D medical scan data set from which accurate measurements can be taken.

According to another aspect, the data set resulting from the combination of the 3D medical scan surface mesh and the dental model provides a complete data set from which treatment can be planned and/or oral surgical appliances can be designed. For example, surgical splints can be manufactured based on accurate images of the surrounding teeth, soft tissue (e.g., nerves, gingival tissue, skin tissue, etc.), and bone structures.

These and other advantages and features, which characterize the present invention, are pointed out with particularity in the claims annexed hereto and forming a further part hereto. However, for a better understanding of the invention, reference should be had to the following drawing and detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In these drawings, like numerals represent like parts throughout the several views:

FIG. 3 is a flowchart illustrating an operational flow for a creation process for producing an electronic dental model of a person's dentition in accordance with the principles of the present disclosure;

FIG. 4 is a flowchart illustrating an operational flow for a first example acquisition process by which the obtain operation of FIG. 3 can be implemented in accordance with the principles of the present disclosure;

FIG. 24 is a front perspective view of another 3D medical scan polygonal mesh constructed based on a second tissue density range from the same cone beam scan as FIG. 23, the 3D medical scan polygonal mesh showing a portion of a patient's skull in accordance with the principles of the present disclosure;

DETAILED DESCRIPTION

As noted above, the principles of the present disclosure provide for a system, method, and apparatus for combining a first set of scanned data with a second set of scanned data to produce a combined set of data. The present disclosure provides for automatic registration between the two data sets by employing a matching technique between the first and second data sets. The accurate portions of each data set can be utilized to reduce the inaccuracies of the other data set. For example, the accuracy of the dental model with respect to teeth occlusal surfaces can be utilized to reduce the inaccuracies of the dentition portion of the cranio-facial 3D medical scan(s).

Preferably, the first set of data includes a dental model—an accurate representation of a patient's dentition (i.e., teeth and soft tissue surrounding the teeth) or portions thereof. As the term is used herein, "patient" can refer to either a human or an animal. The second set of data is initially acquired via a 3D medical scan, such as a cranio-facial CT scan of the patient. Although the cranio-facial scan example will be used throughout this application, it will be appreciated that the principles of the present disclosure can be employed in connection with scans of other parts of the body. For example, the principles can be applied to other objects and/or areas wherein a deficiency is found in taking a 3D medical scan image. The deficiency can be improved by scanning the object and/or area directly or by scanning a casting or impression thereof, and generating a combined image from the combined set of data after registration of the two data sets.

Figure 1:
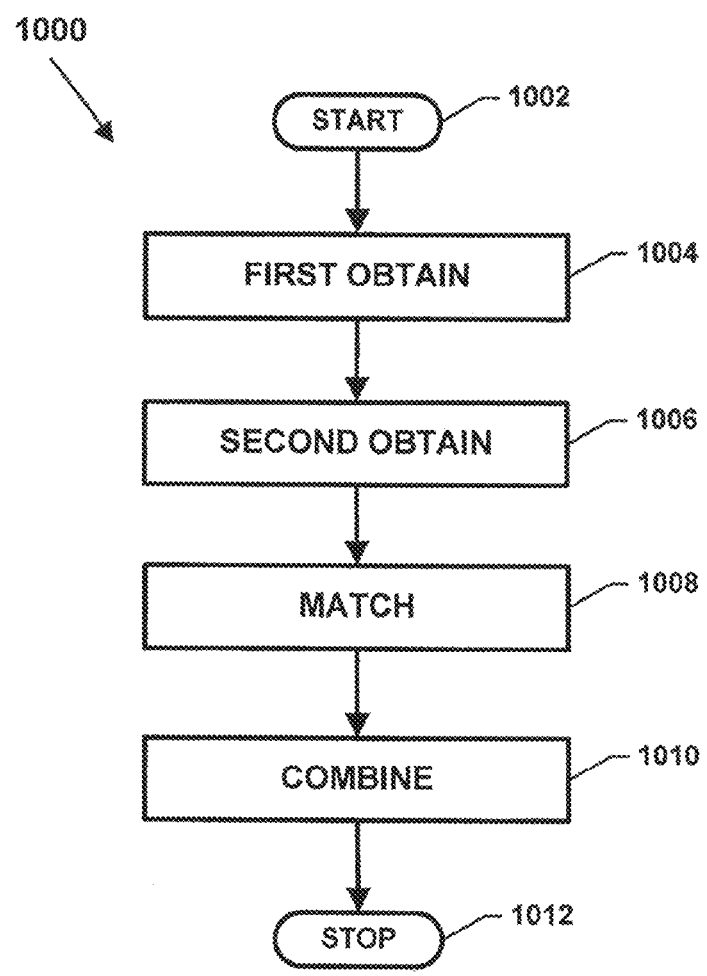
FIG. 1 is a flowchart illustrating an operational flow for an integration process by which a first set of scanned data can be combined with a second set of scanned data in accordance with the principles of the present disclosure.

FIG. 1 is a flowchart illustrating an operational flow for an integration process 1000 by which a first set of scanned data (e.g., a dental model of a patient dentition) can be combined with a second set of scanned data (e.g., a 3D medical scan record). In general, the second set of scanned data is obtained using a different scanning technique than the first set of scanned data. The integration process 1000 performs any appropriate initialization procedures, begins at a start module 1002, and proceeds to a first obtain operation 1004.

The first obtain operation 1004 acquires the first set of scanned data. In general, the first obtain operation 1004 can acquire the first data set using any of a number of scanner devices, such as touch probes, optical scanners, and laser scanners. In some embodiments, the first obtain operation 1004 acquires a first data set representing the dentition of the patient. In such embodiments, the scanner can operate by scanning intra-orally, by scanning an impression of the dentition, and/or by scanning a casting of the dentition. Of course, as noted above, other body parts or objects may be scanned as part of the first obtain step 1004. The acquisition of the first set of scanned data will be discussed in greater detail herein with respect to FIGS. 2-5D.

A second obtain operation 1006 acquires the second set of scanned data. In general, the second obtain operation 1006 acquires the second data set using a 3D medical scanner (e.g., a CT scanner, an MRI scanner, etc.). In one embodiment, the second obtain operation 1006 obtains a cranio-facial scan record using a cone beam scanner. In one embodiment, the second obtain operation 1006 acquires the second data set without including markers or any other type of artificial fiducials or registration points in the second data set. The acquisition of the second set of scanned data will be discussed in greater detail herein with respect to FIG. 6.

A match operation 1008 determines the relationship between the first and second sets of data to prepare for combining the data sets. In one embodiment, the match operation 1008 determines which points, triangles, or other appropriate units in the first and second data sets represent common areas (e.g., the occlusal surfaces of the teeth, surrounding soft tissue, etc.). The matching of the first and second data sets will be discussed in greater detail herein with respect to FIG. 7.

A combine operation 1010 merges the first and second data sets to produce a combined data set from which a composite image can be generated. In some embodiments, the combine operation 1010 merges the data sets so that the combined data set retains only a single set of points for each common area. In one embodiment, the combine operation 1010 determines which of the first and second data sets is a master data set for each common area and eliminates points in the other data set that represent or are otherwise associated with the area. For example, the combine operation 1010 can determine that the representation of teeth occlusal surfaces in the first data set (e.g., the dental model) is more accurate than the representation of the teeth occlusal surfaces in the second data set (e.g., the 3D medical scan). Accordingly, the combine operation 1010 will eliminate the section of the second data set representing the teeth occlusal surface. The merging of the first and second data sets will be discussed in greater detail herein with respect to FIG. 8.

The integration process 1000 performs any appropriate completion procedures and ends at a stop module 1012. In other embodiments, the steps of the integration process 1000 can be implemented in a different order from the one disclosed above. For example, in certain embodiments, the 3D medical scan can be performed prior to obtaining the dental model.

a. Generating the Dental Model

The following section discloses systems and processes by which the first set of scanned data can be acquired in accordance with the first obtain operation 1004 of FIG. 1. Components of one generation system configured to generate the first data set of positional data, which represents a dentition of a patient, include a computing system on which digital models (e.g., polygonal mesh-based electronic models) can be processed and software modules configured to be stored and implemented on the computing system to generate and/or to edit the digital models. The components of the system also include a scanner configured to obtain positional data from an object (e.g., a dentition, an impression thereof, a casting thereof, etc.).

Figure 2:
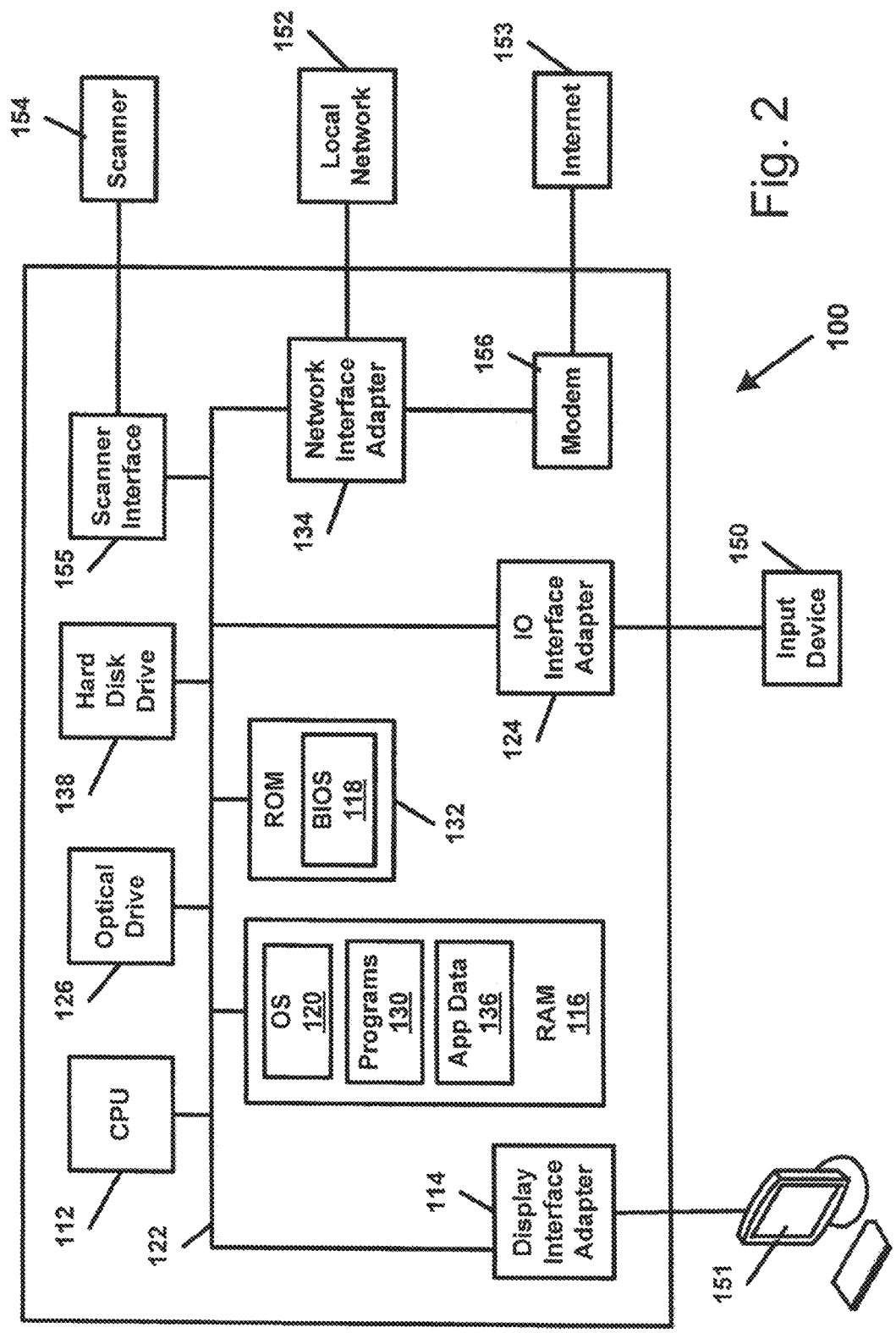
FIG. 2 is a schematic diagram of one example general-purpose computing system for implementing the principles of the present disclosure.

One example computing system on which digital models can be processed is shown in FIG. 2 in the form of a conventional general-purpose, personal computer 100. In other embodiments, however, other types of computing systems (e.g., servers, etc.) can be used. The computer 100 includes a processor unit (CPU) 112, read-only memory (ROM) 132, random access memory (RAM) 116, and a system bus 122 that couples various system components including the RAM 116 to the processor unit 112. The system bus 122 can be any of several types of bus structures, such as a memory bus or memory controller, a peripheral bus, or a local bus using any of a variety of bus architectures. A basic input/output system 118 (BIOS), which contains basic routines that help transfer information between elements within the personal computer 100, is stored in ROM 132.

The computer 100 further includes a hard disk drive 138 for reading from and writing to a hard disk (not shown), a magnetic disk drive (not shown) for reading from or writing to a removable magnetic disk, and an optical disk drive 126 for reading from or writing to a removable optical disk, such as a CD, DVD, or other optical media. The hard disk drive 138, magnetic disk drive, and optical disk drive 126 can be connected to the system bus 122 by a hard disk drive interface (not shown), a magnetic disk drive interface (not shown), and an optical drive interface (not shown), respectively. The drives and their associated computer-readable media provide nonvolatile storage of computer readable instructions, data structures, programs, and other data for the computer 100.

Although the exemplary environment described herein employs a hard disk drive 138, a removable magnetic disk, and removable optical disk drive 126, other types of computer-readable media capable of storing data can be used in the exemplary system. Examples of these other types of computer-readable mediums that can be used in the exemplary operating environment include magnetic cassettes, flash memory cards, digital video disks, Bernoulli cartridges, random access memories (RAMs), and read only memories (ROMs). A number of program modules can be stored on the hard disk drive 138, magnetic disk drive, optical disk drive 126, ROM 332, or RAM 316. For example, an operating system 120, one or more application programs 130, other program modules (not shown), and program (i.e., application) data 136 can be stored on the computer 100.

A user can enter commands and information into the computer 100 through input devices, such as a keyboard and/or mouse 150 (or other pointing device). Non-limiting examples of other input devices can include a microphone, joystick, game pad, satellite dish, touchpad, and scanner. These and other input devices are often connected to the processing unit 112 through an I/O port interface 124 that is coupled to the system bus 122. Nevertheless, these input devices also can be connected by other interfaces, such as a parallel port, a game port, or a universal serial bus (USB). A monitor 151 or other type of display device also can be connected to the system bus 122 via an interface, such as a video adapter 114. In addition to the monitor, personal computers typically include other peripheral output devices (not shown), such as speakers and printers.

The computer 100 can operate in a networked environment using logical connections to one or more remote computers or other devices (e.g., scanner, fabricator, etc.). The remote computer can be a personal computer, a server, a router, a network PC, a peer device, or other common network node. The network connections can include a local area network (LAN), a wide area network (WAN), an enterprise-wide computer network, an intranet, and the Internet. When used in a LAN networking environment, the computer 100 is connected to the local network 152 through a network interface or adapter 134. When used in a WAN networking environment, the computer 100 typically includes a modem 156 or other means for establishing communications over the wide area network, such as the Internet 153. The modem 156, which can be internal or external, is connected to the system bus 122 via the network interface adapter 134. In a networked environment, program modules depicted relative to the computer 100 or portions thereof can be stored in remote memory storage device. It will be appreciated that the network connections shown are exemplary only and other means of establishing a communications link between computers can be used.

Portions of the preferred embodiment constructed in accordance with the principles of the present disclosure utilize a computer and are described herein as implemented by logical operations performed by a computer. The logical operations of these various computer implemented processes are generally performed either (1) as a sequence of computer implemented steps or program modules running on a computing system and/or (2) as interconnected machine modules or hardware logic within the computing system. The sequence of computer implemented steps or program modules can be stored on a suitable computer readable medium from which the computing system can read and implement the steps/modules. The implementation is a matter of choice dependent on the performance requirements of the computing system implementing the invention. Accordingly, the logical operations making up the embodiments of the invention described herein can be variously referred to as operations, steps, or modules.

A scanner 154 can be connected to the computer 100 via an appropriate scanner interface 155. The scanner interface 155 can be connected to the system bus 122 such that the scanned data can be stored in the appropriate or desired memory location, manipulated by the CPU 112, displayed on the display 151, etc. In one embodiment, the scanner 154 includes a laser line scanner arranged and configured for scanning dental study casts. For example, the scanner 154 can include a laser line scanner from the Surveyor WS-Series of line scanners, manufactured by Laser Design Inc. of Minneapolis, Minn. However, in other embodiments, any suitable scanner (e.g., laser scanner, optical scanner, touch-probe scanner, etc) can be used and a number of other methodologies might be employed to generate the scanned image data.

FIG. 3 is a flowchart illustrating an operational flow for a creation process 200 for producing an electronic dental model of a patient's dentition in accordance with the principles of the present disclosure. In one embodiment, the creation process 200 can be implemented using the computer 100 and scanner 154 of FIG. 2. The creation process 200 performs any appropriate initialization procedures, begins at a start module 202, and proceeds to an obtain operation 204.

The obtain operation 204 acquires or otherwise receives positional data indicating the location and/or dimensions of a dentition of a patient. In one embodiment, the obtain operation 204 scans a physical model (e.g., a casting of a dentition) or other representation of the dentition of the patient to obtain positional data from which to generate an electronic model. In another embodiments, the obtain operation 204 can perform an intra-oral scan of the patient's dentition to obtain positional data. In other embodiments, the obtain operation 204 can acquire positional information using other types of acquisition methodologies, such as optical system scanning and physical touch scanning. In still other embodiments, the obtain operation 204 can retrieve a previously generated electronic model from a database or from another computing system.

A generate operation 206 creates at least one electronic model of the dentition based on the acquired positional data. For example, in certain embodiments, a polygonal mesh model can be generated. In certain embodiments, the generate operation 206 produces multiple electronic models based on the acquired positional data. In one embodiment, the generate operation 206 produces first and second electronic models of the dentition. For example, the generate operation 206 can produce a maxillary dentition model and a mandibular dentition model. In another embodiment, the generate operation 206 can produce a different dental model for each tooth of the patient. In other embodiments, however, the generate operation 206 produces only a single electronic model based on the acquired positional data.

In some embodiments, the generate operation 206 can convert scan data points representing a negative image (e.g., of an impression) to a positive image (e.g., of the dentition), thereby creating a digital model based on the positive image. One non-limiting example of a commercially available software package that can be used to generate three-dimensional images from scanned positional data is the package sold under the designation Geomagic Studio from Geomagic, Inc. in Research Triangle Park, N.C. In other embodiments, however, the generate operation 206 can generate a dental model representing a negative image based on negative image scan data.

An optional remove operation 208 enables removal of a portion of the dental model. For example, in one embodiment, when an impression or casting of a dentition is scanned, the impression or casting can include an artificial base to provide stability to the impression or casting without representing any portion of the patient's dentition. In other case, data points acquired during an intra-oral scan can include data representing a greater region of the patient's dentition or mouth than was intended to be obtained. The remove operation 208 enables identification of a section of the dental model (e.g., the base of a casting) to be deleted and elimination of the identified section from the dental model.

An optional display operation 210 presents the generated electronic model to a user. For example, the display operation 210 can present the electronic model on a monitor 151 (FIG. 2) or other output device. In one embodiment, the display operation 210 can display the electronic model at a fixed position and/or orientation. In another embodiment, the display operation 210 can facilitate transforming (e.g., rotating and/or translating) the electronic model to enable viewing of all sides of the electronic model. In one embodiment, the electronic model can be converted into a file format acceptable to a three-dimensional graphic image manipulation software program (e.g., an ".STL" format). For example, 3d Studio by AutoDesk, Inc. of San Rafael, Calif. might be employed to view and manipulate the image.

A storage operation 212 enables the user to store the electronic model as a permanent record of the baseline condition of the patient's teeth. For example, the storage operation 212 can enable the user to save the electronic model to storage media (e.g., hard disk drive 138, optical drive 126, RAM 116, or ROM 132) on a computer, such as computer 100 (FIG. 2). In another embodiment, the storage operation 212 can enable the user to store the electronic model on a remote computer or remote storage device. For example, the storage operation 212 can enable the user to transmit the electronic model over a network to the remote computer or storage device.

The creation process 200 completes and ends at a stop module 214. Further details describing the acquisition and generation of the electronic dental model of the dentition are discussed below.

FIG. 4 is a flowchart illustrating an operational flow for a first example acquisition process 300 by which the obtain operation 204 of FIG. 3 can be implemented. While the acquisition is described in the context of obtaining a dentition impression, it is contemplated that impressions of other parts of a patient's body also can be taken. The acquisition process 300 performs any appropriate initialization procedures, begins at a start module 302, and proceeds to an obtain operation 304. The obtain operation 304 takes a dental impression of a person's dentition.

For example, the patient can bite down into an impression tray filled with impression material, which hardens, thereby forming a negative image of the teeth. In one embodiment, the obtain operation 304 takes two dental impressions using a mandibular impression tray and a maxillary impression tray to obtain a mandibular impression and a maxillary impression. In certain embodiments, the obtain operation 304 also can take a bite impression (e.g., using a bite/clutch tray) to obtain a bite record indicating a correct spatial orientation and relationship between the maxillary and mandibular impressions.

An optional cast operation 306 fabricates a casting of the patient's dentition based on the obtained dental impression. In certain embodiments, the cast operation 306 fabricates a first casting of the patient's mandible based on the mandibular impression and fabricates a second casting of the patient's maxilla based on the maxillary impression. In some embodiments, the cast operation 306 can separately cast various components of the patient's dentition. For example, in one embodiment, the cast operation 306 can separately fabricate each of the teeth on the patient's mandible so that the fabricated teeth can be removably attached to a casting of the patient's mandible.

A mount operation 308 secures the obtained impression or the fabricated casting to a scanner. In one embodiment, the mount operation 308 secures the obtained impression or the fabricated casting to a laser line scanner. In some embodiments, the mount operation 308 secures the impression or casting to a base of the scanner at a fixed position and orientation. In other embodiments, the mount operation 308 secures the impression or casting to the scanner so as to enable rotation of the impression or casting to facilitate scanning the entire impression or casting.

A scan operation 310 acquires positional information pertaining to the obtained impression or fabricated casting. In certain embodiments, the scan operation 310 can acquire positional information pertaining to multiple impressions or castings. By scanning the teeth or physical representation thereof directly with a line scanner, high resolution and speed are gained. In one embodiment, the scan operation 310 can obtain a first scan of a mandibular impression or casting and can obtain a second scan of a maxillary impression or casting. In certain embodiments, the scan operation 310 can acquire positional information on the bite record in order to properly reference together the two sets of data acquired in the scans. One example scanning methodology used by a laser line scanner is generally described in U.S. Pat. No. 5,124,524, which is hereby incorporated herein by reference.

The acquisition process 300 completes and ends at a stop module 312.

Referring now to FIGS. 5A-5D, one example process for implementing the generate operation 206 of FIG. 3 to generate electronic dental models of dentitions from scanned positional data points will be briefly described. When a laser line scanning device or other suitable scanner passes a sensor over a surface of a physical model (e.g., an impression, a casting, the dentition itself), the scanning device obtains an array of points corresponding to a surface line on the physical model.

Figure 5A:
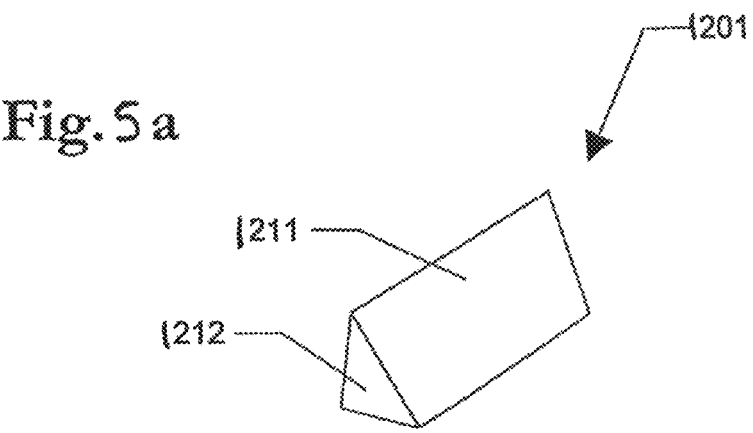
FIGS. 5A-5D are schematic diagrams illustrating the generation of a dental model from scanned positional data points in accordance with the principles of the present disclosure.
Figure 5B:
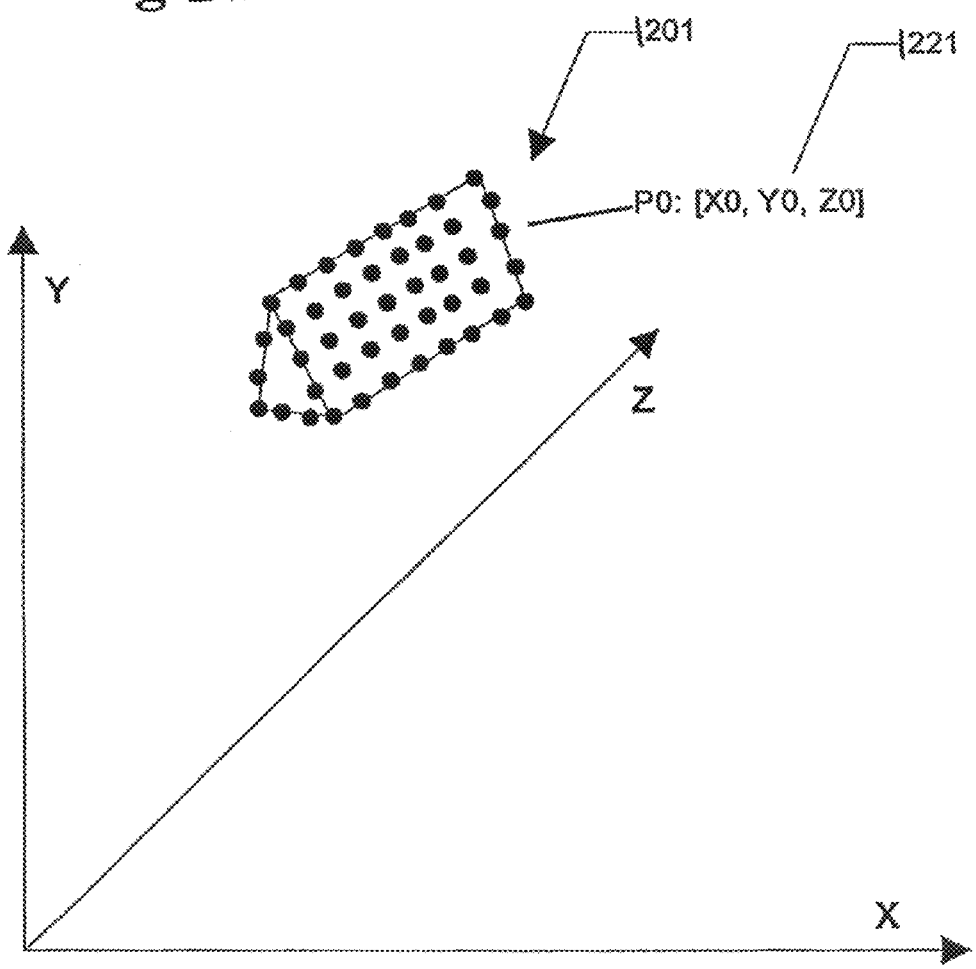

FIG. 5A shows a physical object 1201 in the shape of a prism. A first surface 1211 and a second surface 1212 of the prism 1201 are visible in FIG. 5A. FIG. 5B shows positional data points 1221 obtained by scanning the first surface 1211 and the second surface 1212 of the physical object 1201 with a laser line scanner. Of course, in various embodiments, the scanning device can obtain positional data points for the entire exterior of the object 1201 or only select portions or surfaces of the object 1201. The position of each of these data points 1221 can be specified within a three-dimensional space using a three-coordinate position P={X, Y, Z}.

As the scanning device laser is moved within a scanning area of a multi-axis base platform, the scanning device translates the acquired data points 1221 to a coordinate system of the scanning device. Accordingly, the collection of all obtained data points represents the points in a 3D coordinate system that corresponds to the scanned surfaces 1211, 1212 of the model 1201. In one embodiment, these data points 1221 are stored within a point cloud data file. It will be appreciated that only a first data point 1221 is explicitly shown as point P0 in FIG. 5B. However, undesignated points also are illustrated. Each of the other points can be identified as described in connection with FIG. 5C below.

Figure 5C:
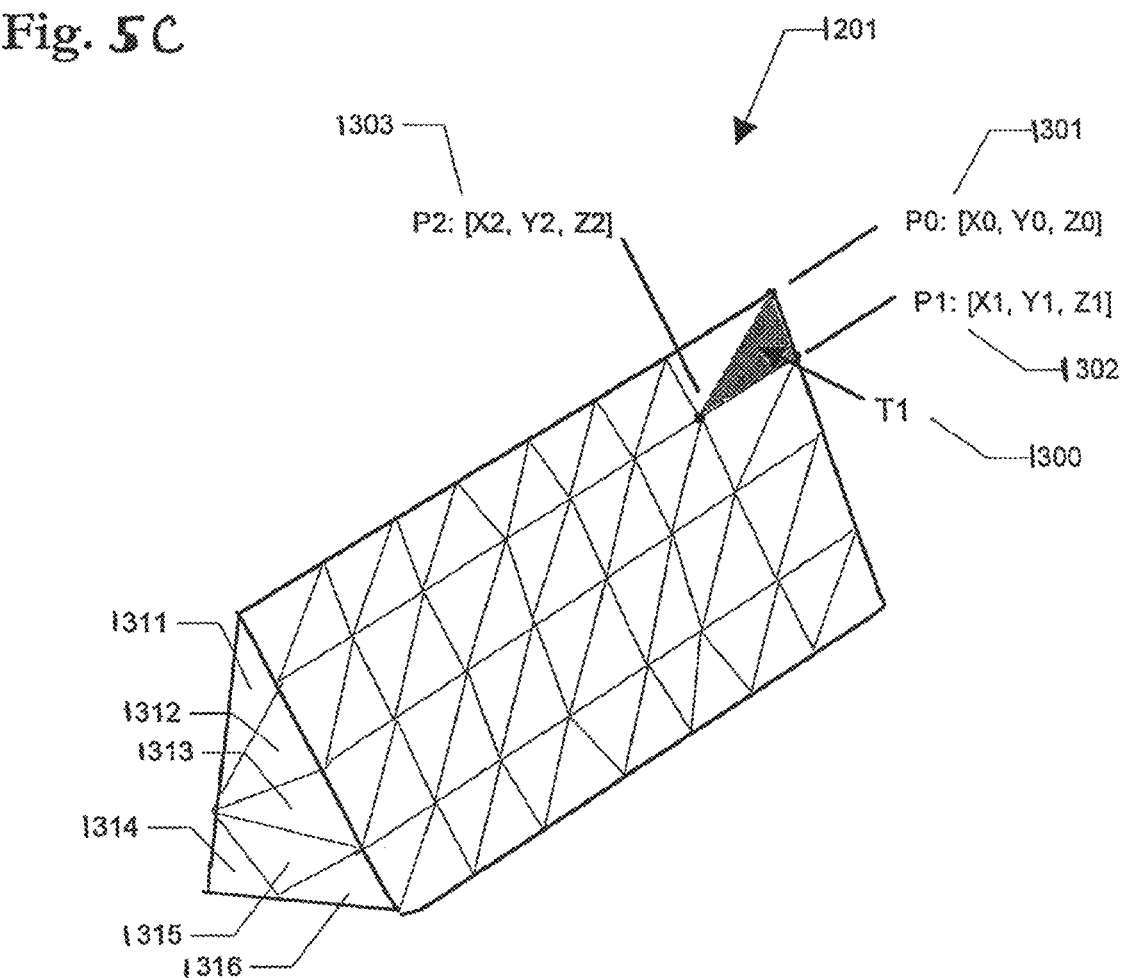

Referring now to FIG. 5C, the obtained positional data points (e.g., the point cloud data file) are reduced to an initial polygonal mesh 1300 of triangles in which the surfaces of the triangles are used to approximate the surfaces 1211, 1212 of the physical model 1201. Each triangle in the initial polygonal mesh 1300 is specified using three points P0, P1, P2 corresponding to its three corners. For example, triangle T1 is specified using points P0 1301, P1 1302, and P2 1303 such that T1={P0, P1, P2}={[X0, Y0, Z0], [X1, Y1, Z1], [X2, Y2, Z2]}. The triangles in the initial polygonal mesh can be created using any number of well-known methods for converting point position data into a polygonal mesh that approximates the surface of an object. In other embodiments, the point cloud data file can be reduced to a polygonal mesh of other types of polygons.

Figure 5D:
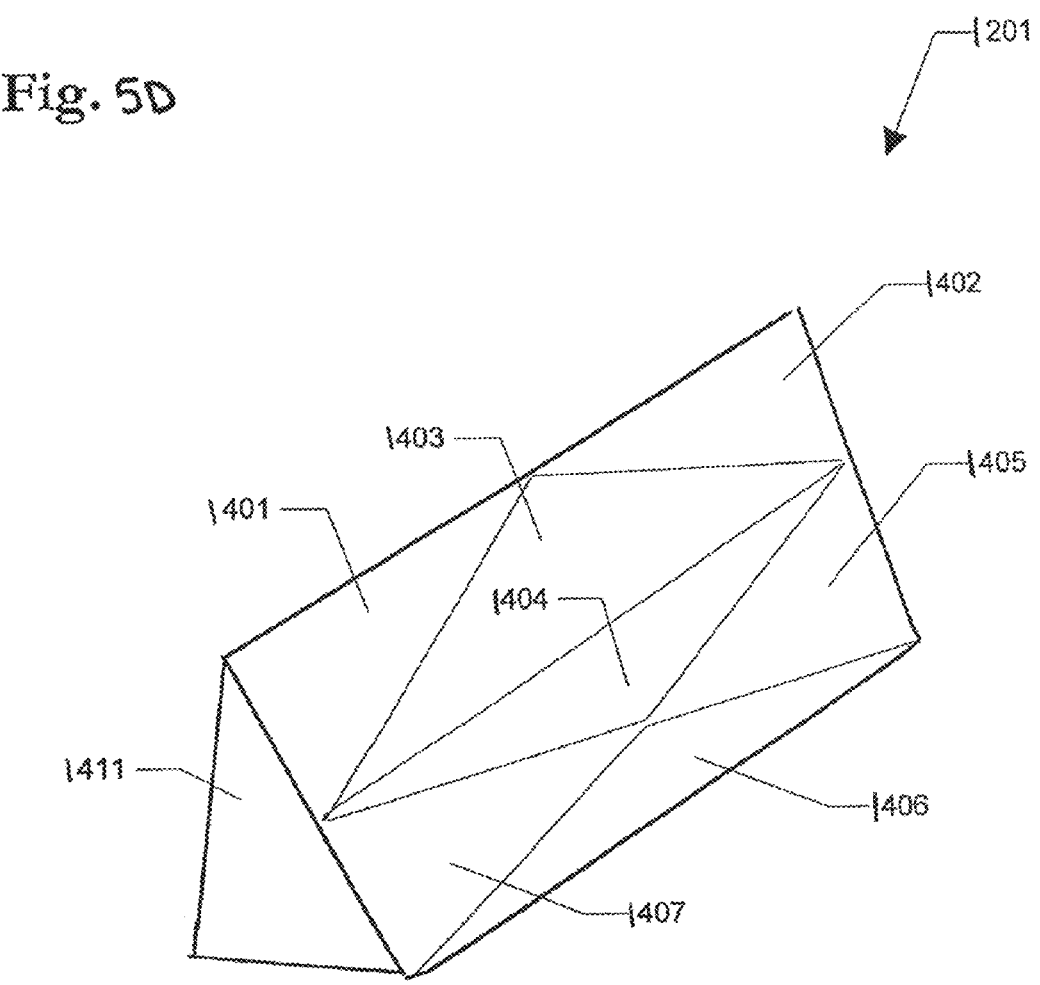

In FIG. 5D, a reduced polygonal mesh 1400 can be generated by combining adjacent triangles in the initial polygonal mesh 1300 when two or more triangles are sufficiently coplanar that they can be represented using a single triangle. For example, triangles 1311-1316 in FIG. 5C are reduced to triangle 1411 in FIG. 5D. Triangles 1421-1427, which define the side surface of the electronic model, are also shown in FIG. 5D. The processing associated with this filtering operation controls the number of triangle combination by setting a threshold relating to the minimum amount of deviation from a single plane for two or more triangles that is permitted before the two or more triangles are required to remain separate. This filtering process can be accomplished using a number of commercially available polygonal mesh processing products.

b. Generation of the 3D Medical Scan Record

The following section discloses systems and processes by which the second set of scanned data can be acquired in accordance with the second obtain operation 1006 of FIG. 1. Three-dimensional scanners have been developed that provide three-dimensional imaging that can be used to create one or more digital representations of a patient's body or portions thereof, such as the patient's cranio-facial region. Alternatively, a digital representation of the patient's body or portions thereof can be obtained using two-dimensional scanners that obtain a sequence of two-dimensional images from which one or more three-dimensional image can be constructed.

Examples of such scanners include cone beam tomography scanners, CAT scanners, MRI scanners, and other technologies that provide three-dimensional digital models or images from which a three-dimensional model can be constructed. Examples of commercially available scanners include cone beam scanners sold under the trade names ILUMA® from IMTEC® Corporation of Ardmore, Okla. and i-CAT® from Imaging Sciences International of Hatfield, Pa. Advantageously, some medical scanners are able to image not only the dentition of the patient, but also the surrounding bone structure and soft tissue (e.g., nerves, gingival tissue, skin tissue, etc.).

Figure 6:
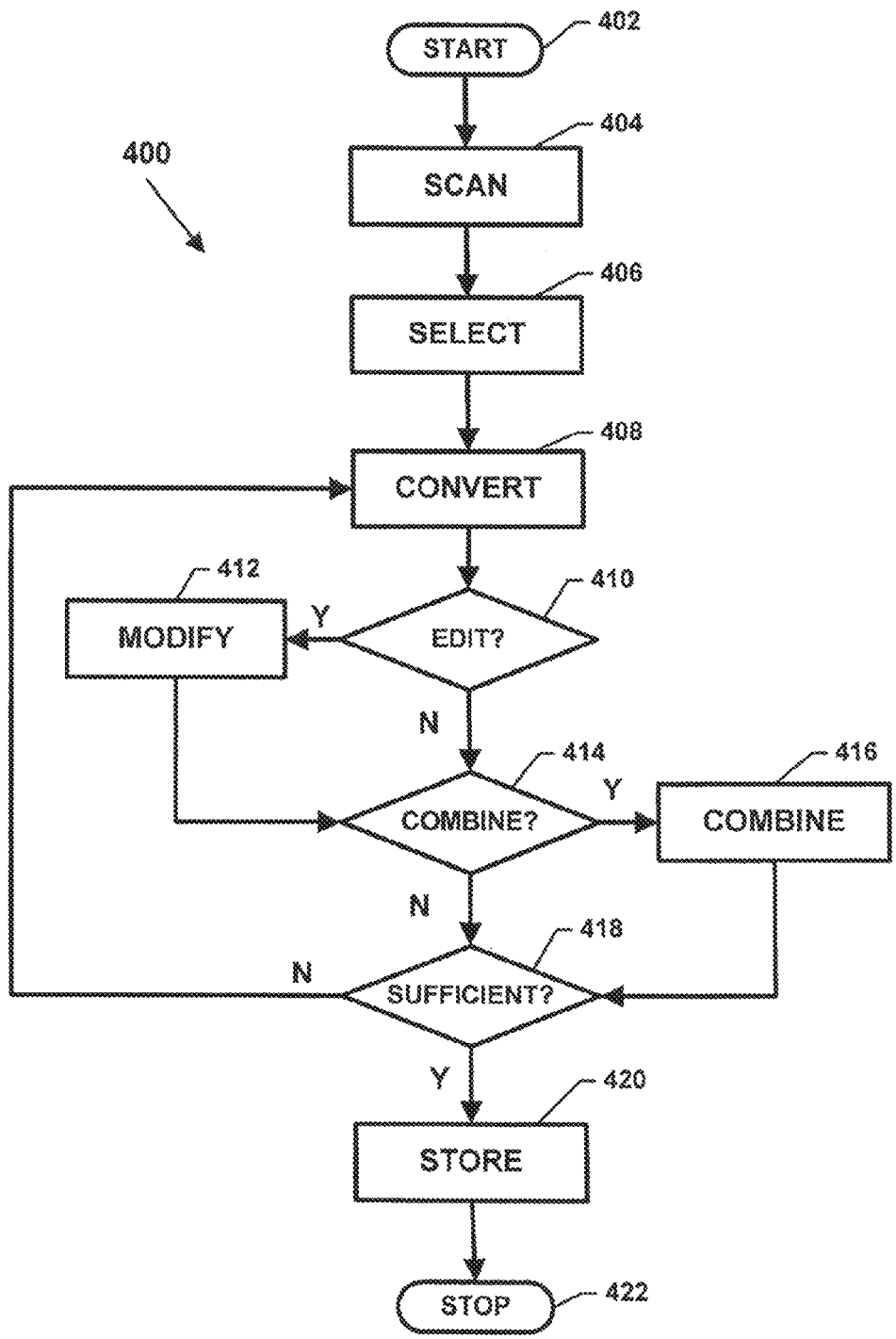
FIG. 6 is a flowchart illustrating a second example acquisition process by which the second obtain operation of FIG. 1 can be implemented in accordance with the principles of the present disclosure.

FIG. 6 is a flowchart illustrating an example second acquisition process 400 by which the second obtain operation 1006 of FIG. 1 can be implemented. The second acquisition process 400 performs any appropriate initialization procedures, begins at a start module 402, and proceeds to a scan operation 404. The scan operation 404 acquires positional data of an object (e.g., a cranio-facial region of a patient) using a scanner, such as one of the CT scanners disclosed above. In one embodiment, the scan operation 404 acquires positional data of one or more teeth of a patient. In another embodiment, the scan operation 404 also acquires positional data for the surrounding bone structure and/or soft tissue.

Figure 20:
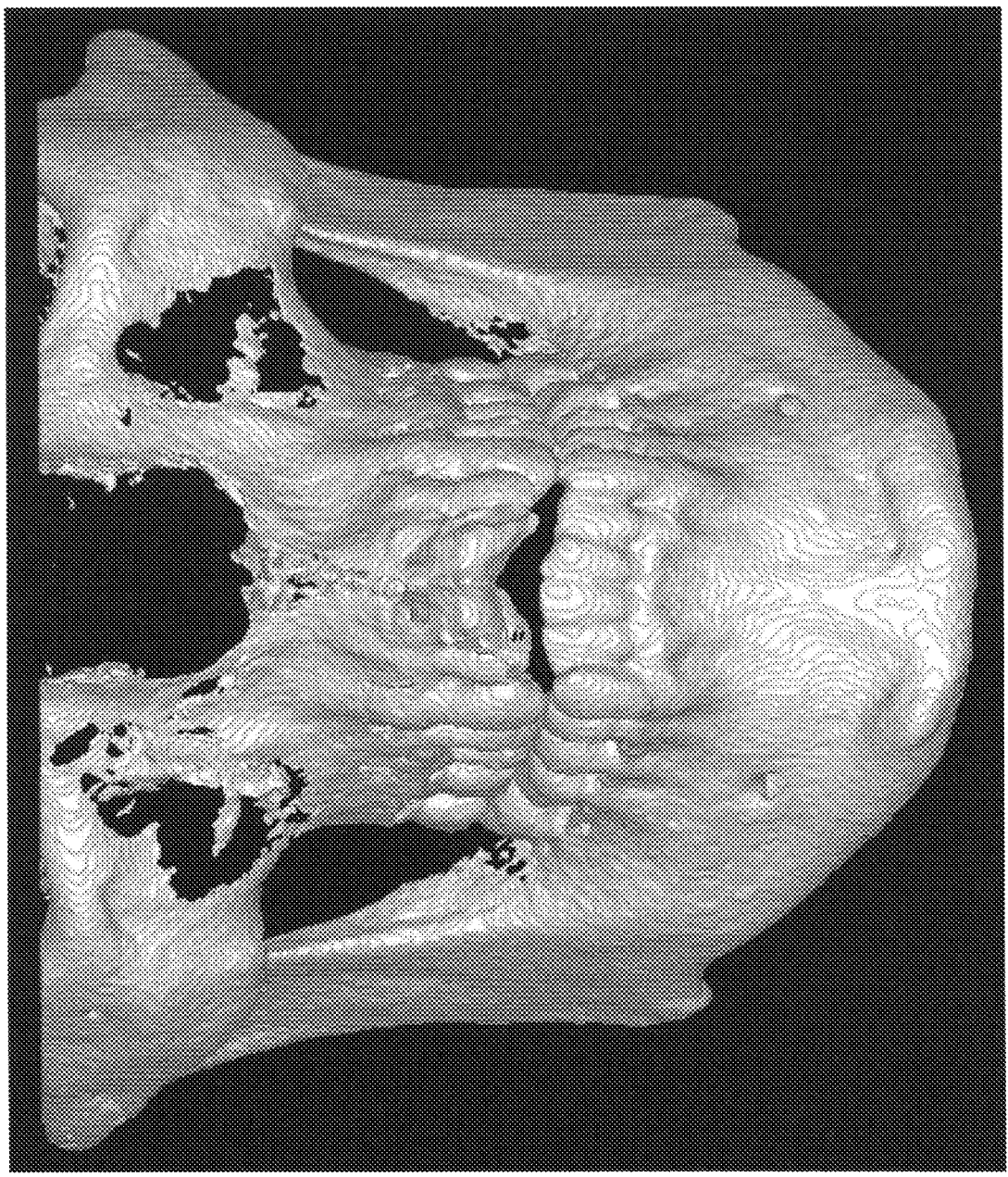
FIG. 20 is a front elevational view of a first 3D medical scan polygonal mesh generated based on a CT scan viewed at a first tissue density range in which teeth of the patient are visible in accordance with the principles of the present disclosure.
Figure 21:
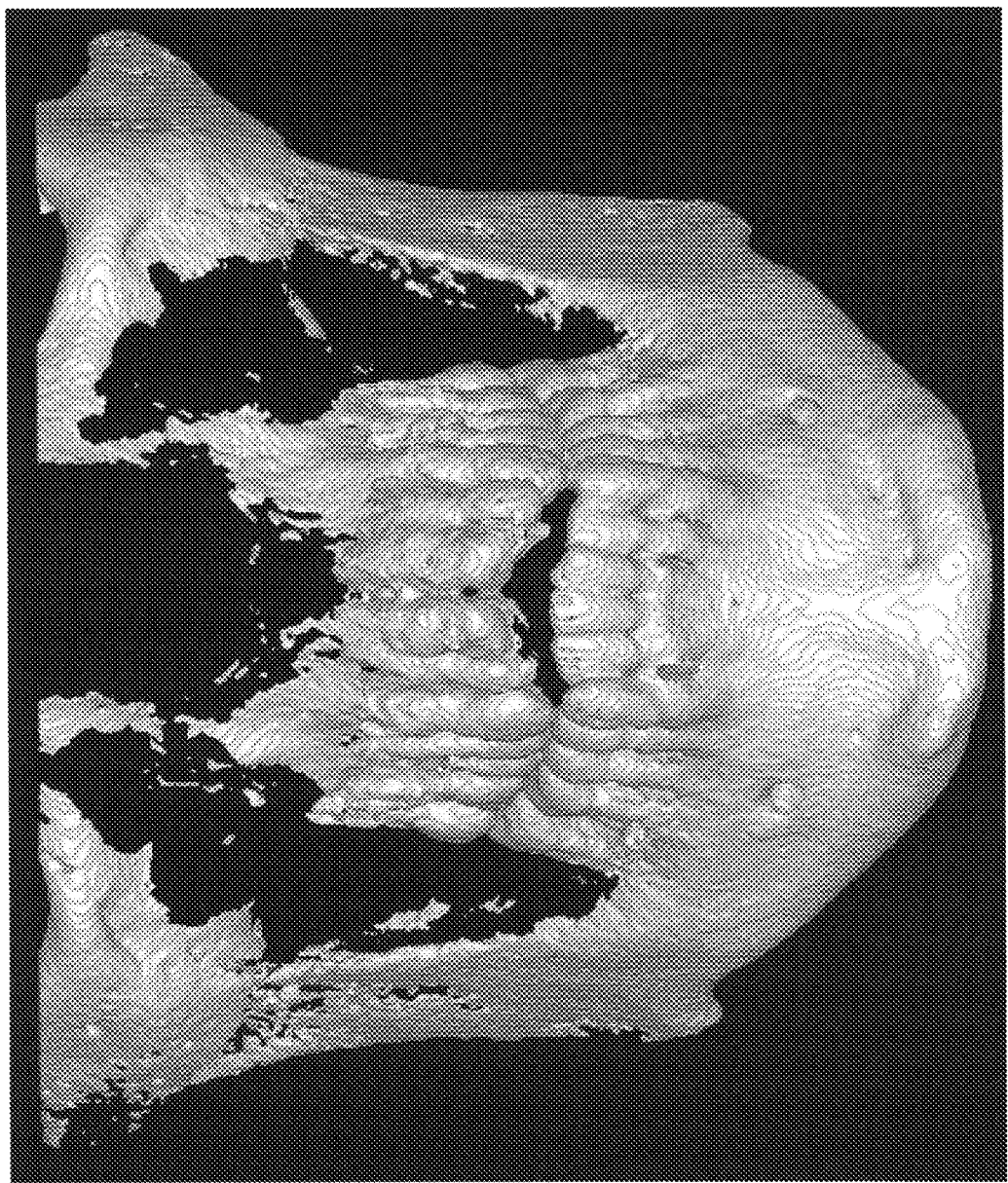
FIG. 21 is a front elevational view of a second 3D medical scan polygonal mesh generated based on the same 3D medical scan as FIG. 21 viewed at a second tissue density range in which roots of the teeth are visible in accordance with the principles of the present disclosure.
Figure 22:
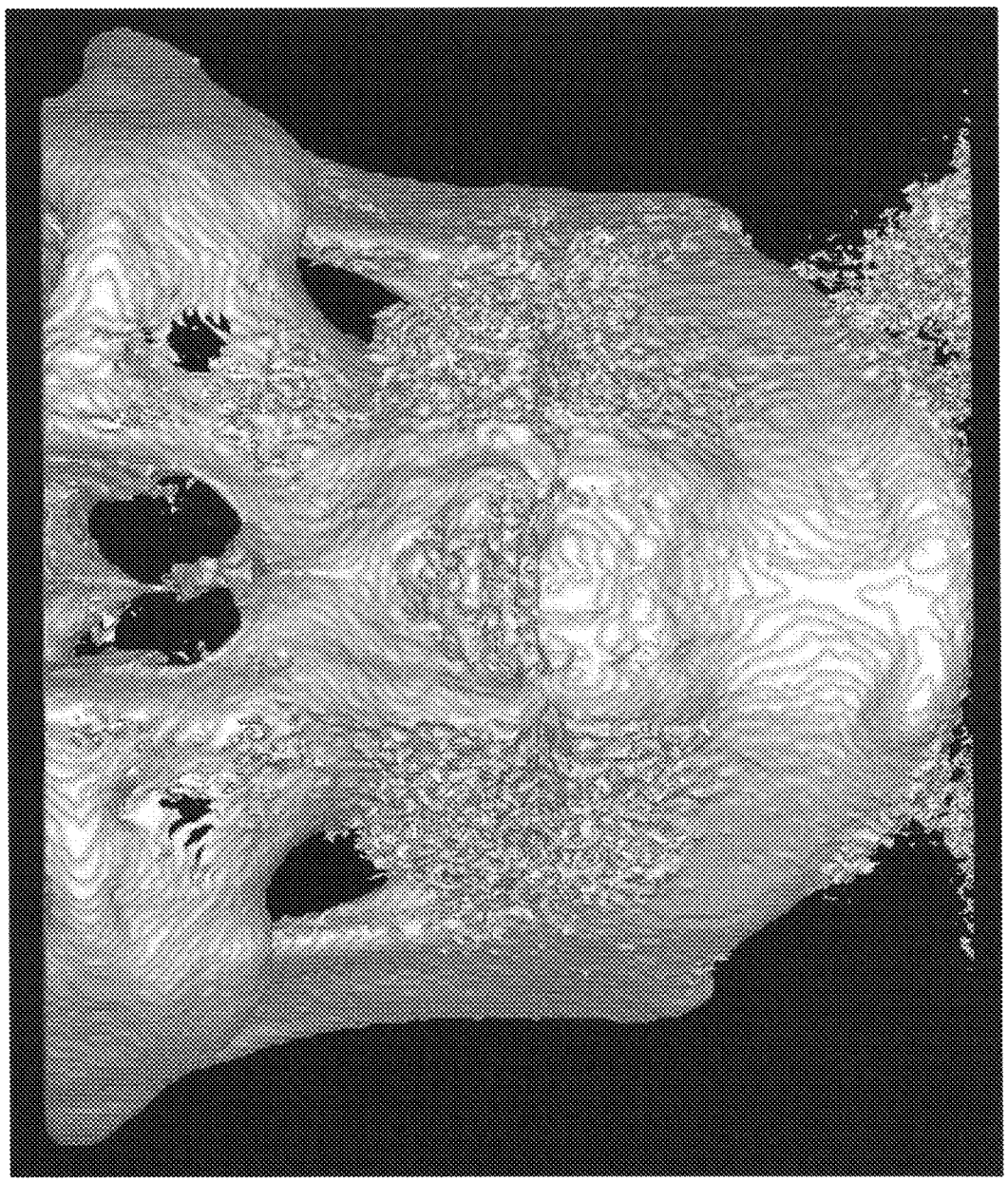
FIG. 22 is a front elevational view of a third 3D medical scan polygonal mesh generated based on the same 3D medical scan as FIG. 21 viewed at a third tissue density range in which joints of the patient are visible in accordance with the principles of the present disclosure.

A select operation 406 enables a user to determine an appropriate tissue density range (i.e., threshold) at which to view the acquired positional data. In general, different anatomical features are best displayed at various tissue densities of a CT or MRI scan. Users can select different ranges of tissue densities at which to view the acquired positional data. For example, in one embodiment, teeth of a patient can be best viewed at a first tissue density (see FIG. 20), roots of the patient's teeth can be best seen at a second tissue density (see FIG. 21), and joints (e.g., condyles) of the patient can be best seen at a third tissue density (see FIG. 22).

A convert operation 408 modifies the acquired positional data into a surface mesh (e.g., a polygonal mesh) electronic model for the selected tissue density. This conversion can be accomplished by utilizing a commercially available algorithm. For example, in one embodiment, the convert operation 408 can be accomplished using the "Voxel Meshing Module" software available from the National Alliance for Medical Image Computing (www.na-mic.org). In another embodiment, the convert operation 408 can be accomplished using the "Reconstruct 1.0" software by Gerhard Roth at the Institute for Information Technology at the National Research Council of Canada in Ottawa, Canada.

A first determination module 410 determines whether to edit the polygonal mesh electronic model. For example, the first determination module 410 can determine whether to separate a first portion of the surface mesh from a second portion of the surface mesh. If the first determination module 410 determines the polygonal mesh should not be modified, then the acquisition process proceeds to a second determination module 414. If the first determination module 410 determines that at least a portion of the mesh should be modified, however, then a modify operation 412 edits the polygonal mesh. For example, the modify operation 412 can enable a user to remove a base of the impression or casting from the polygonal mesh image of the impression or casting.

In certain embodiments, the modify operation 412 enables a user to select mesh points manually using an input tool. The modify operation 412 then allows the user to move, isolate, and or delete the mesh points. In other embodiments, the modify operation 412 selects mesh points automatically based on an algorithm. For example, in one embodiment, the modify operation 412 can separate a first portion of the surface mesh representing the mandible of a person from a second portion of the surface mesh representing the maxilla of the person. Separating portions of the mesh enables the portions to be manipulated independently. In one embodiment, a mandible can be moved separately from a maxilla to simulate movement of the jaw (e.g., chewing). In another embodiment, a section of bone (e.g., in the mandible) can be removed to simulate and/or aid in planning a surgical procedure. In yet another embodiment, inaccurate sections of the polygonal mesh can be eliminated.

The second determination module 414 determines whether multiple surface mesh models have been generated and, if so, whether the mesh models should be combined into a single mesh model. If only one mesh has been generated or if two mesh models are desirable, then the acquisition process 400 proceeds to a third determination module 418. Two or more mesh models can be desirable to enable movement of an object (e.g., a mandible) represented in one polygonal mesh relative to objects (e.g., a maxilla) represented in the other polygonal meshes. Furthermore, maintaining separate mesh models facilitates the retention of the obtained positional data. Retaining this data enable the user to selectively view one or more of the models simultaneously to show the same area at different tissue densities.

Figure 30:
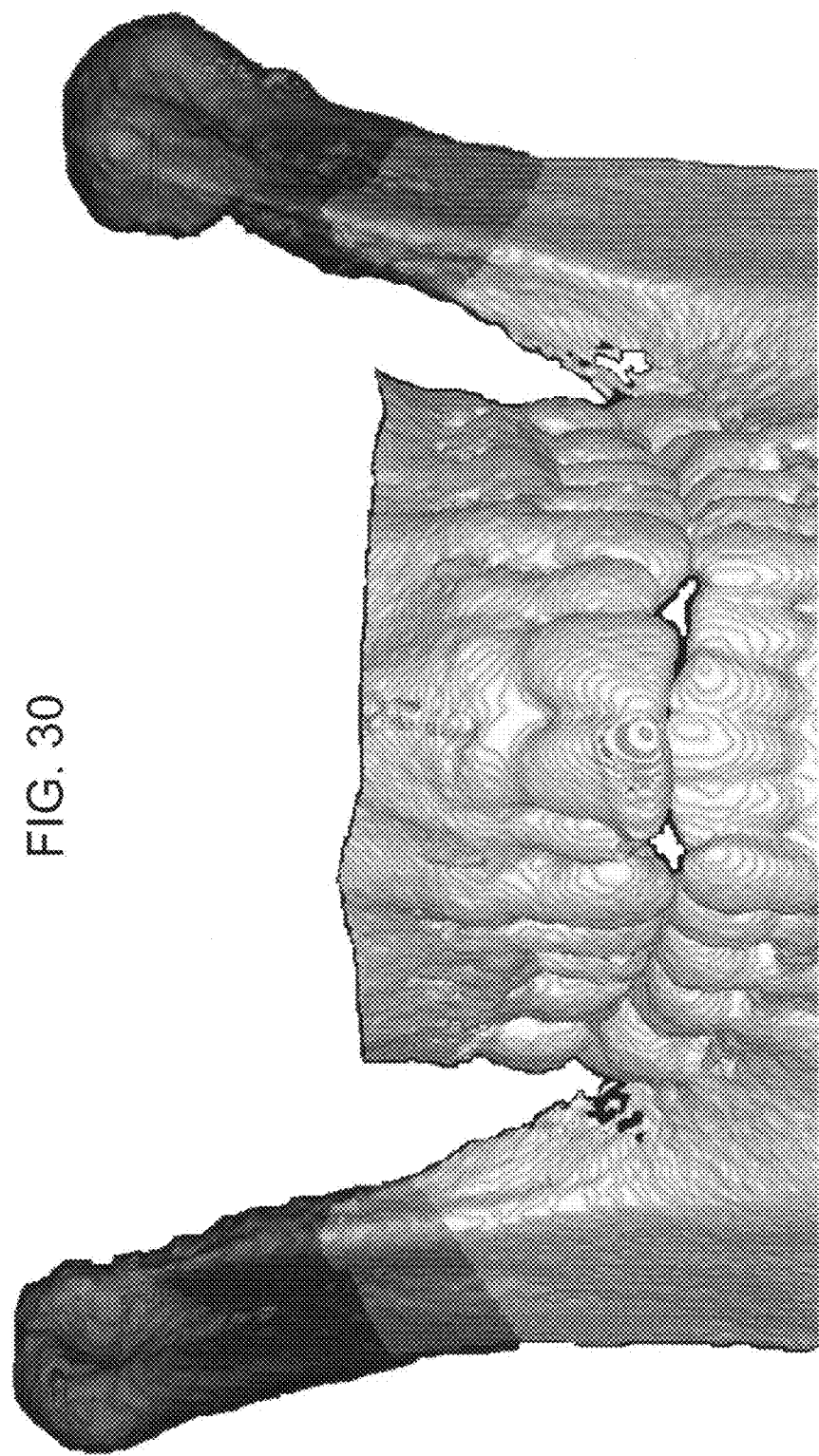
FIG. 30 is a partial facial view of three 3D medical scan polygonal meshes representing the mandible of a patient, the three 3D medical scan polygonal meshes superimposed together in accordance with the principles of the present disclosure.
Figure 31:
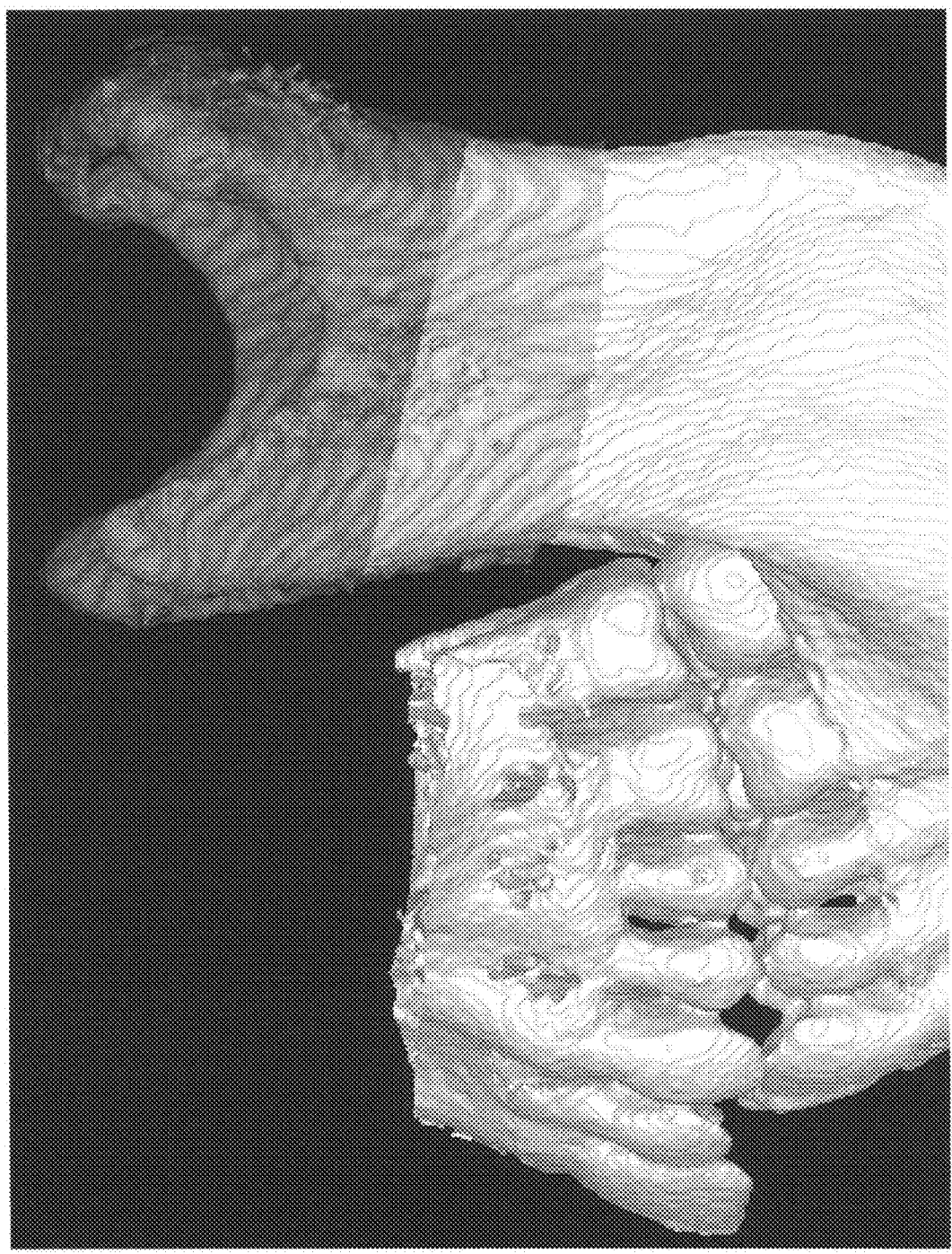
FIG. 31 is a left side elevational view of the three 3D medical scan polygonal meshes of FIG. 30.
Figure 32:
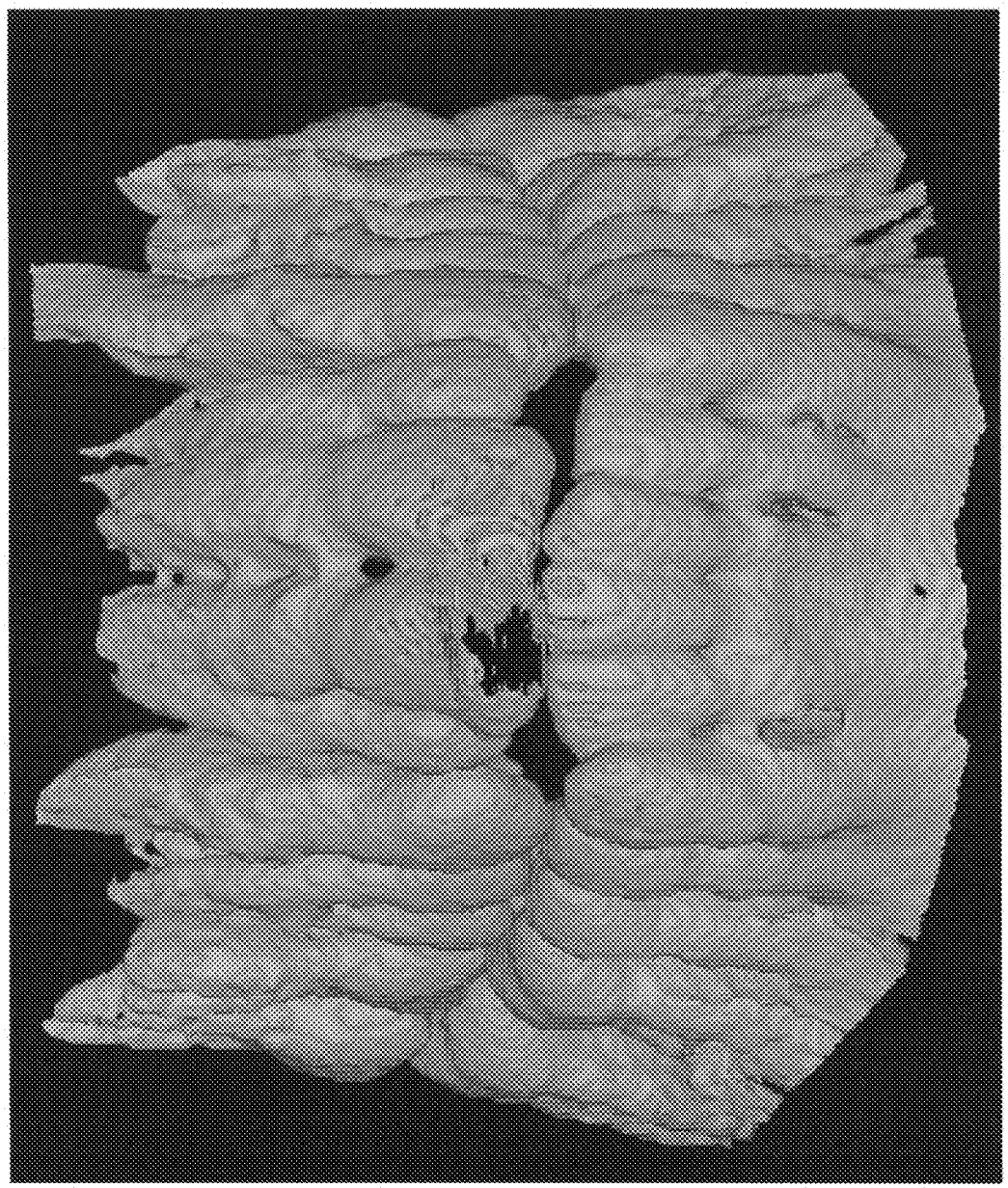
FIG. 32 is a facial view of a 3D medical scan polygonal mesh representing teeth and roots of a patient at a first tissue density in accordance with the principles of the present disclosure.
Figure 33:
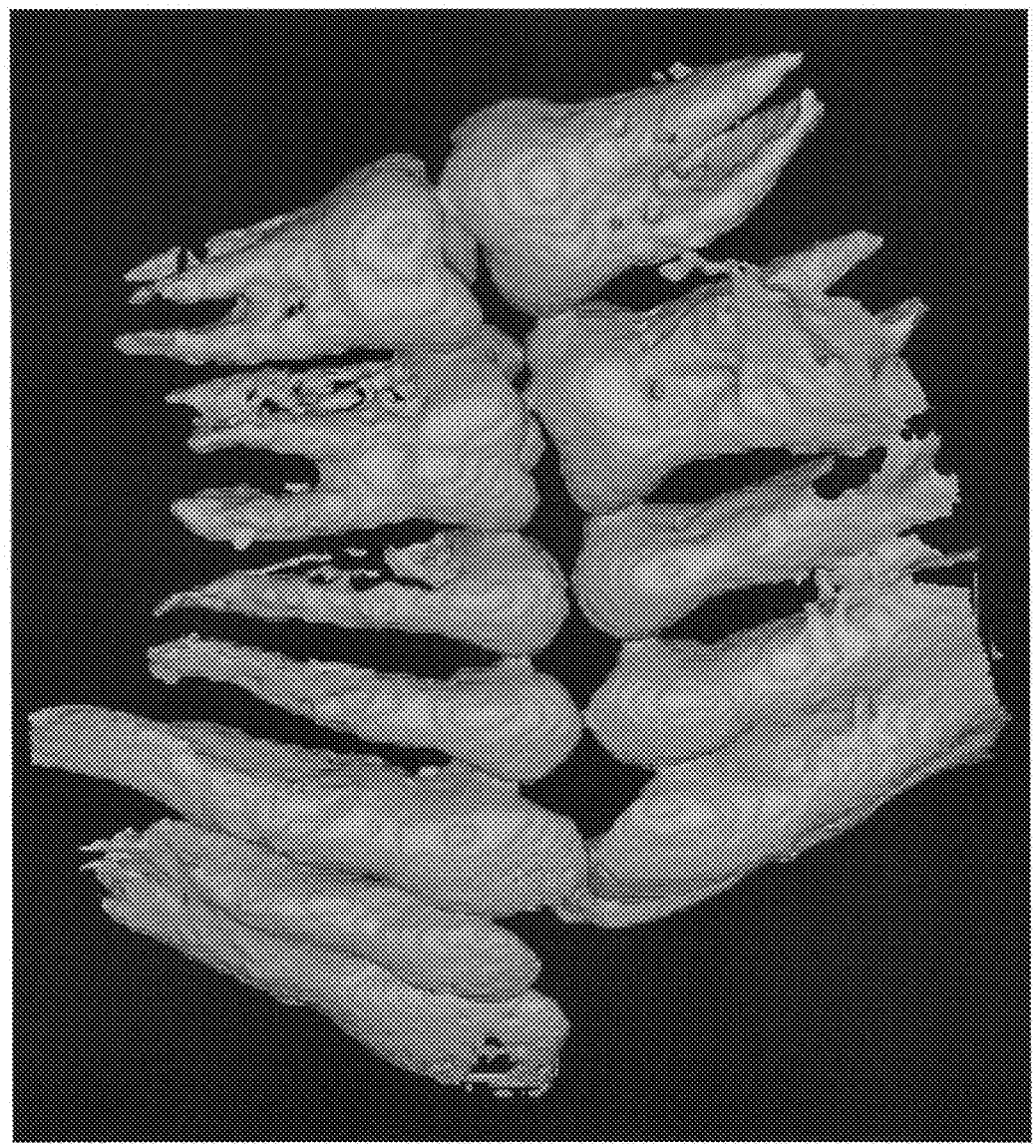
FIG. 33 is a left-side elevational view of the polygonal mesh of FIG. 32 in accordance with the principles of the present disclosure.
Figure 34:
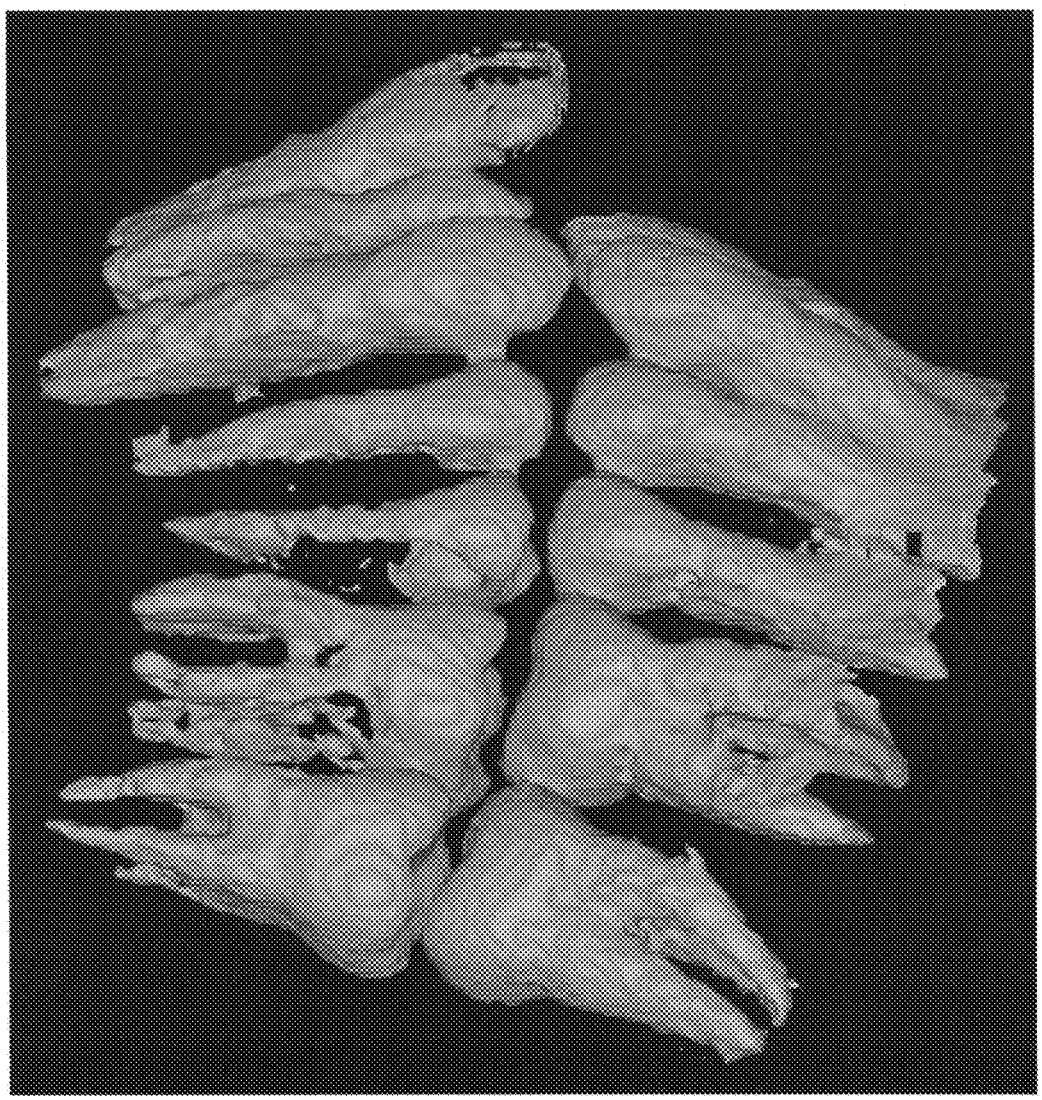
FIG. 34 is a right-side elevational view of the polygonal mesh of FIG. 32 in accordance with the principles of the present disclosure.
Figure 35:
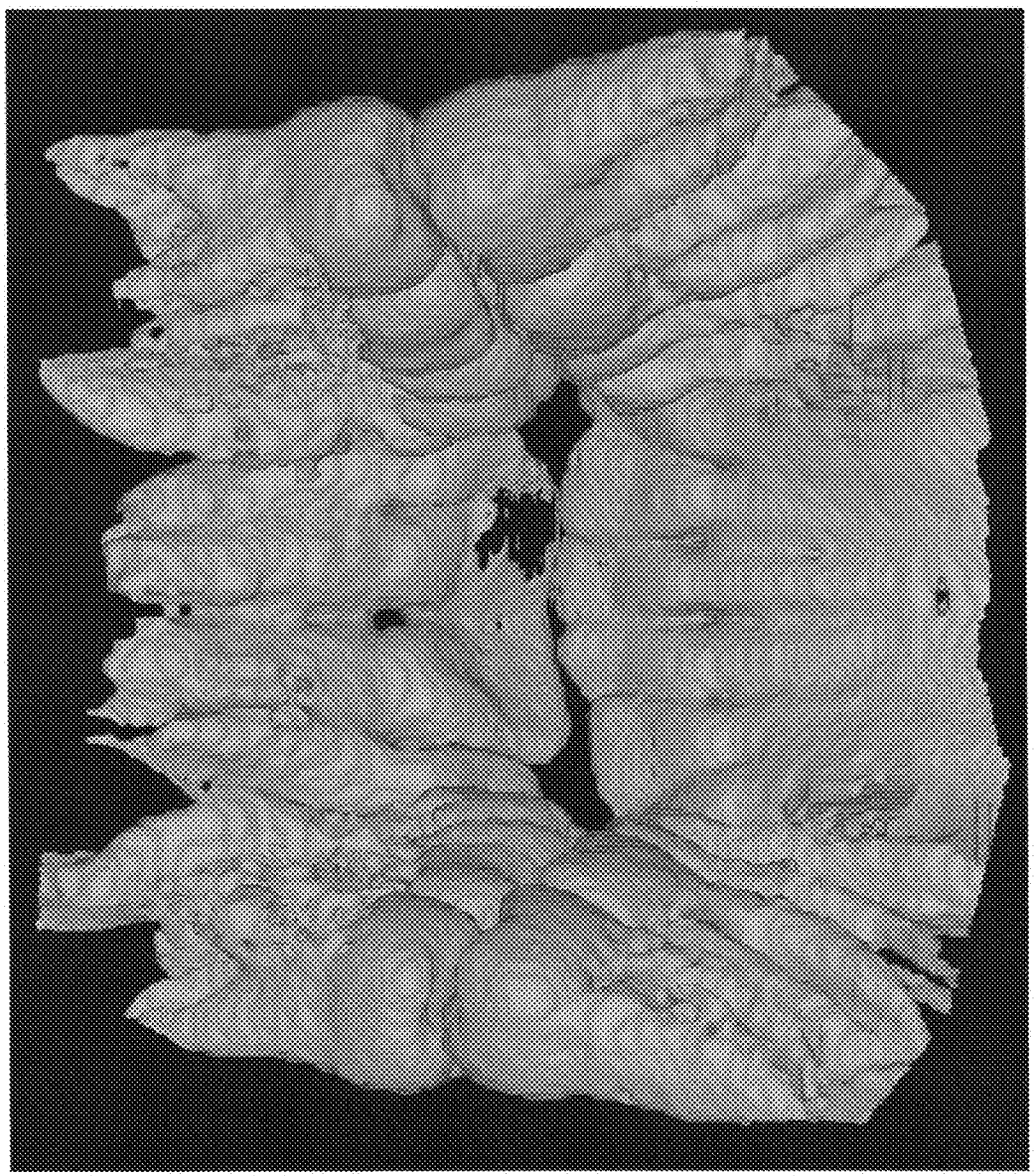
FIG. 35 is a lingual view of the polygonal mesh of FIG. 32 in accordance with the principles of the present disclosure.

FIGS. 26-29 each shows a different view of an example polygonal mesh in which three different polygonal meshes of three different tissue densities are superpositioned together to form a 3D medical scan. For clarity, each polygonal mesh is illustrated in a different color, shading, or texture (e.g., see FIG. 28). FIGS. 30 and 31 each show a different view of another example polygonal mesh in which three different polygonal meshes of three different tissue densities are superpositioned together. For example, In FIGS. 30 and 31, a first polygonal mesh represents the mandible of the patient; a second polygonal mesh represents bone structure nearer the condyles of the patient; and a third polygonal mesh represents the condyles of the patient. Therefore, if it is desirable for a user to view condyle from the first tissue density, then the second and third polygonal meshes can be removed from sight.

Figure 23:
FIG. 23 is a front perspective view of a 3D medical scan polygonal mesh constructed based on a first tissue density range from a cone beam scan, the 3D medical scan polygonal mesh showing a portion of a patient's skull in accordance with the principles of the present disclosure.
Figure 25:
FIG. 25 is a front perspective view of a combined 3D medical scan polygonal mesh constructed by combining the polygonal mesh of FIG. 23 with the polygonal mesh of FIG. 24 in accordance with the principles of the present disclosure.
Figure 26:
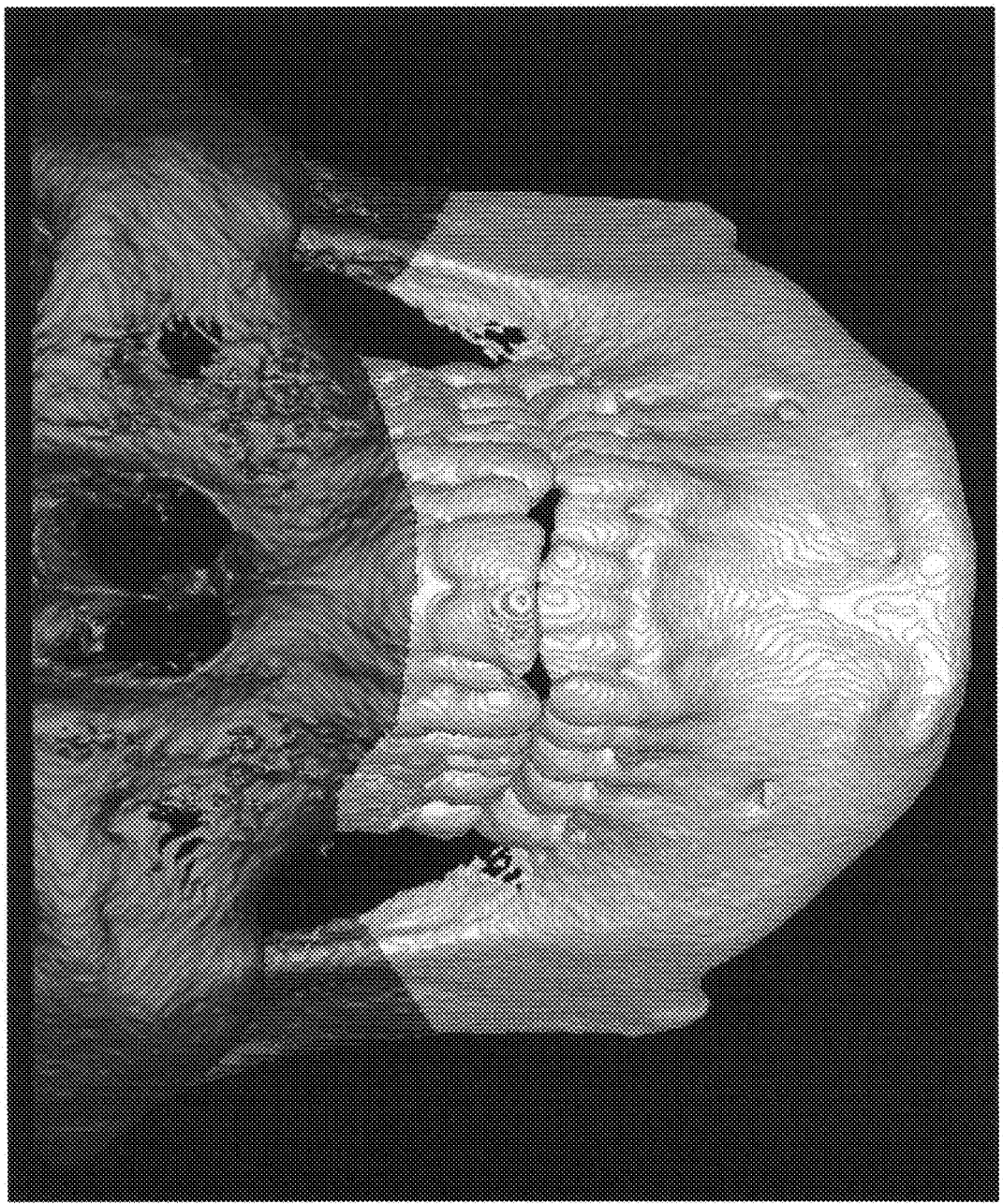
FIG. 26 is a facial view of a 3D medical scan polygonal mesh representing a lower portion of a patient's cranio-facial region, the 3D medical scan polygonal mesh including a first section representing the region at a first tissue density, a second section representing the region at a second tissue density, and a third section representing the region at a third tissue density in accordance with the principles of the present disclosure.
Figure 27:
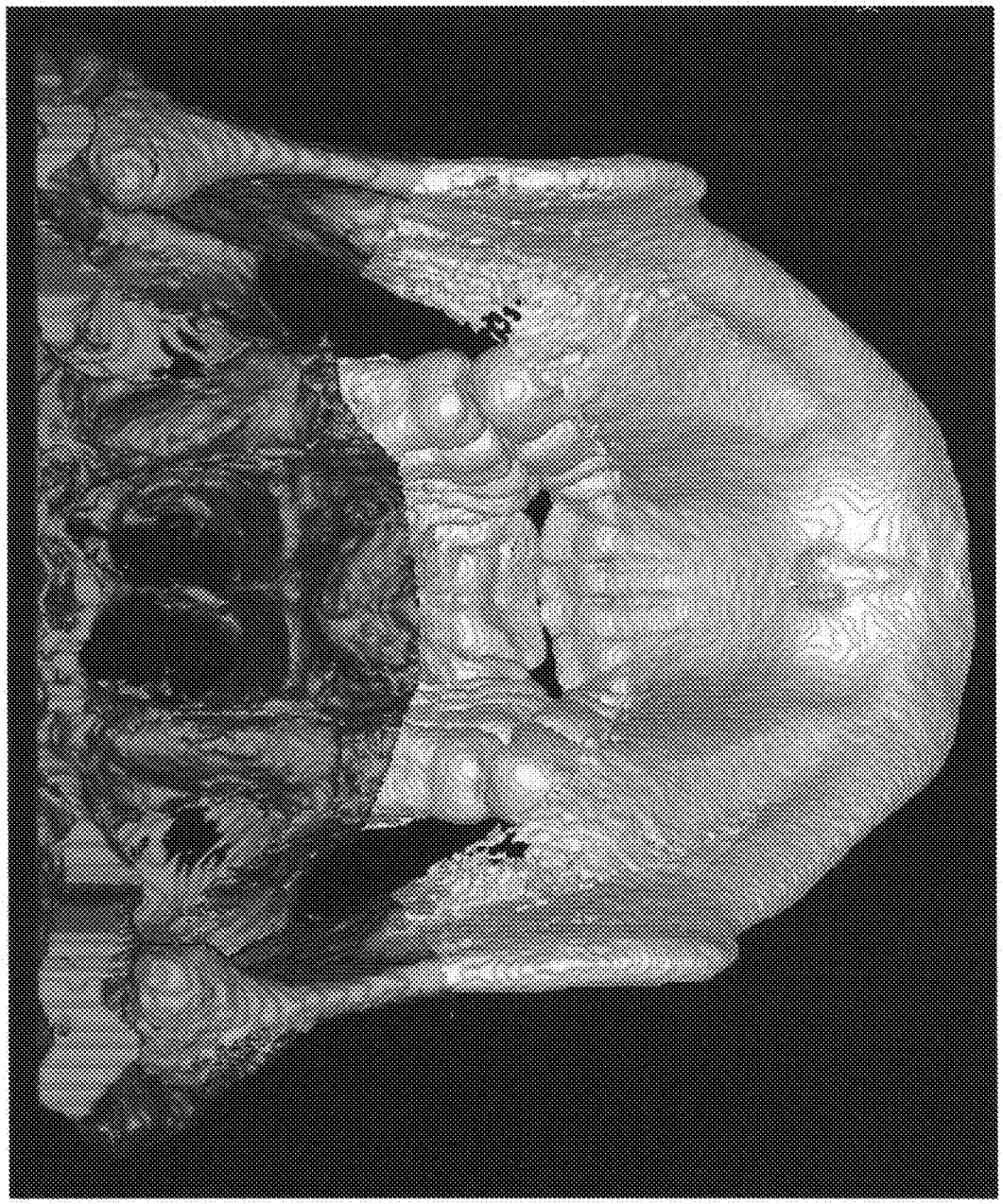
FIG. 27 is a lingual view of the 3D medical scan polygonal mesh of FIG. 26 in accordance with the principles of the present disclosure.
Figure 28:
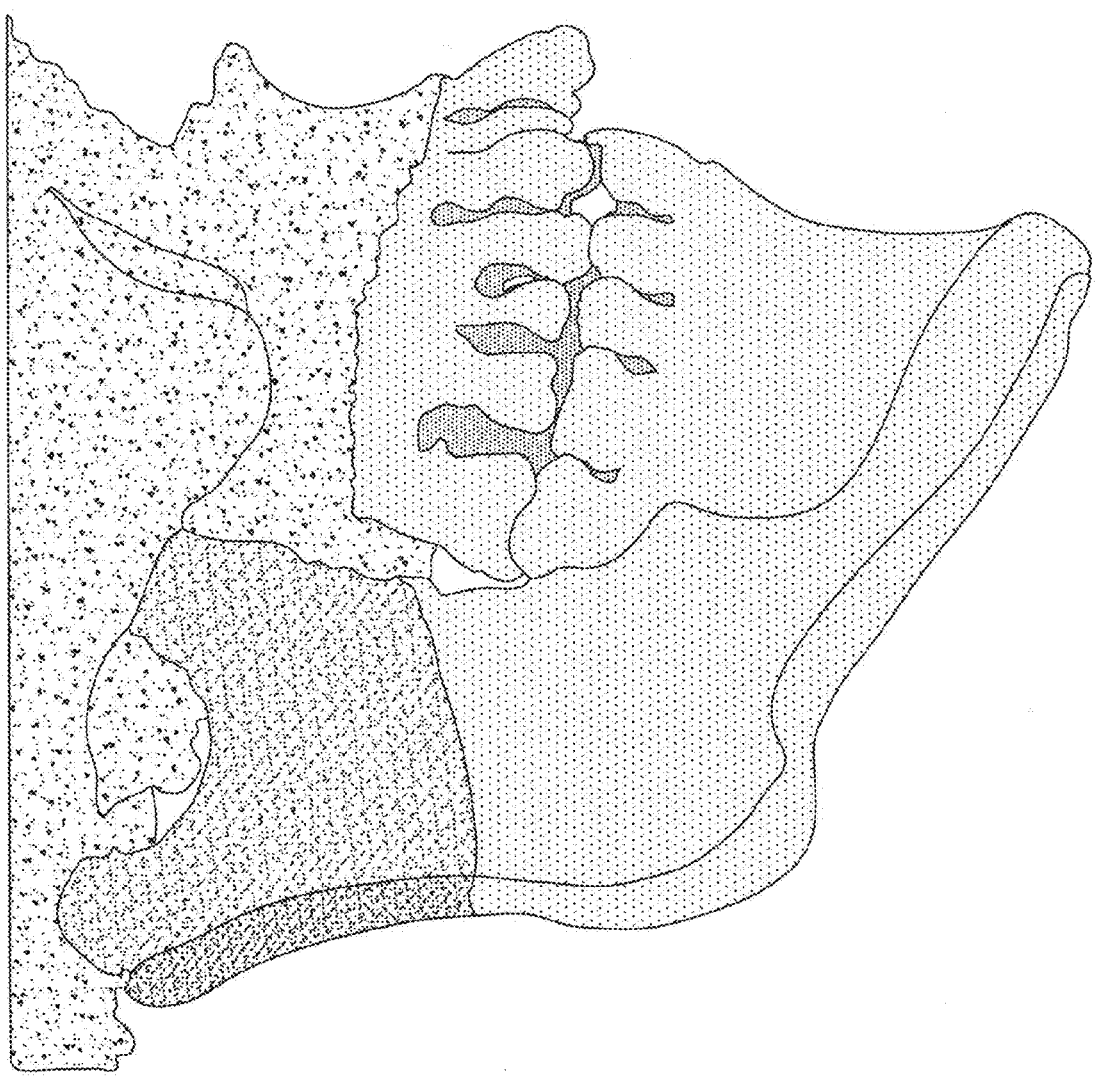
FIG. 28 is a right side elevational view of the 3D medical scan polygonal mesh of FIG. 26 in accordance with the principles of the present disclosure.
Figure 29:
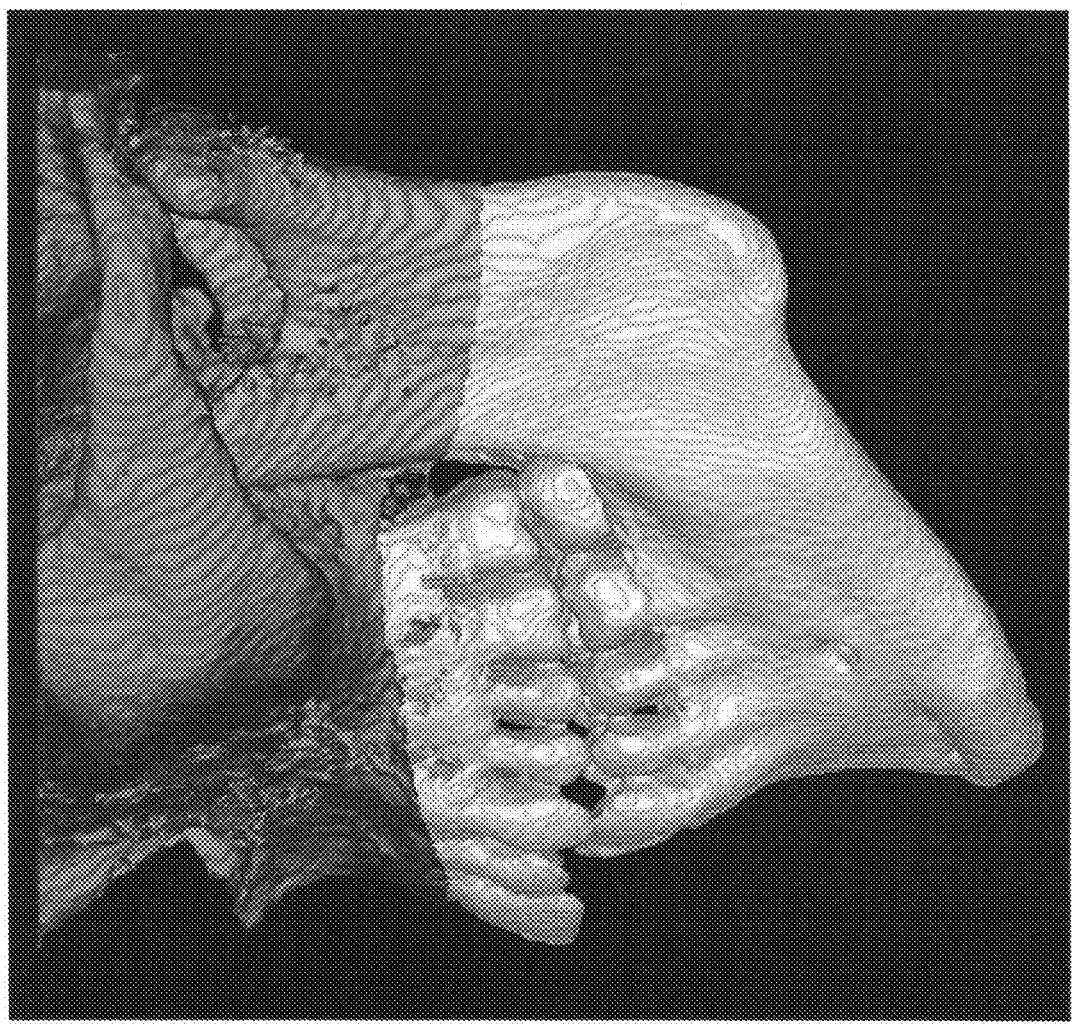
FIG. 29 is a left side elevational view of the 3D medical scan polygonal mesh of FIG. 26 in accordance with the principles of the present disclosure.

If two or more surface mesh models have been generated and it is desirable to combine them, however, then a combine operation 416 can combine the surface mesh models into a single surface mesh module. For example, FIG. 23 shows a first polygonal mesh constructed based on a first tissue density from a cone beam scan of a portion of a patient's jaw. FIG. 24 shows a second polygonal mesh constructed based on a second tissue density from the cone beam scan. The second polygonal mesh provides better accuracy/clarity of a portion of the anatomical features represented in the first polygonal mesh. Accordingly, the first and second polygonal meshes can be combined as shown in FIG. 25.

FIGS. 26-29 illustrate different views of another example polygonal mesh in which three different polygonal meshes of three different tissue densities are combined. A first of the polygonal meshes represents the mandible of the patient; a second of the polygonal meshes represents the condyles of the patient; and a third of the polygonal meshes represents the maxilla of the patient. For clarity, each polygonal mesh is illustrated in a different color. In other embodiments, greater or fewer numbers of polygonal meshes can be combined into a single mesh. For example, in one embodiment, an additional polygonal mesh representing a tissue density at which the roots of the patient's teeth are visible can be added to the combined polygonal mesh (e.g., see FIGS. 32-35).

The acquisition process 400 then proceeds to the third determination module 418. The third determination module 418 determines whether the converted polygonal mesh or meshes represent the area to be scanned with sufficient accuracy. If the third determination module 418 determines the polygonal mesh is sufficiently complete, then the acquisition process 400 proceeds to a store operation 420. If the third determination module 418 determines the polygonal mesh is not sufficiently complete, however, then the acquisition process 400 cycles back to the select operation 406 and begins again.

For example, in one such embodiment, the select operation 406 selects a different tissue density at which to view the positional data obtained from the 3D medical scan to more clearly see data missing from the converted mesh model. The convert module 408 generates a new polygonal mesh based on the different tissue density selection. Since the same positional data is used, the new polygonal mesh model will have the same coordinate system as the previous polygonal mesh model. The first determination operation 410 determines whether to edit the new polygonal mesh and the modify operation 412 edits the polygonal mesh as appropriate. The second determination module 414 indicates that multiple surface meshes have been generated and elects to combine the meshes. The combine operation 416 combines the new polygonal mesh with the previous polygonal mesh to form a combined mesh. The acquisition process 400 continues to cycle back to the select operation 406 until the third determination module 418 determines the polygonal mesh is sufficiently accurate.

The store operation 420 enables storage of the second data set (i.e., the polygonal mesh or meshes resulting from the 3D medical scan record) as a permanent or semi-permanent record of the condition of the patient's cranio-facial region. For example, the store operation 420 can enable a user to save the second data set to storage media (e.g., a hard disk drive 138, an optical drive 126, RAM 116, ROM 132, etc.) on a computer, such as computer 100 (FIG. 2). In another embodiment, the store operation 420 can enable the user to store the second data set on a remote computer or remote storage device. For example, the store operation 420 can enable the user to transmit the second data set over a network to the remote computer or storage device.

The second acquisition process 400 completes and ends at a stop module 422.

c. Matching the Two Electronic Records

Figure 7:
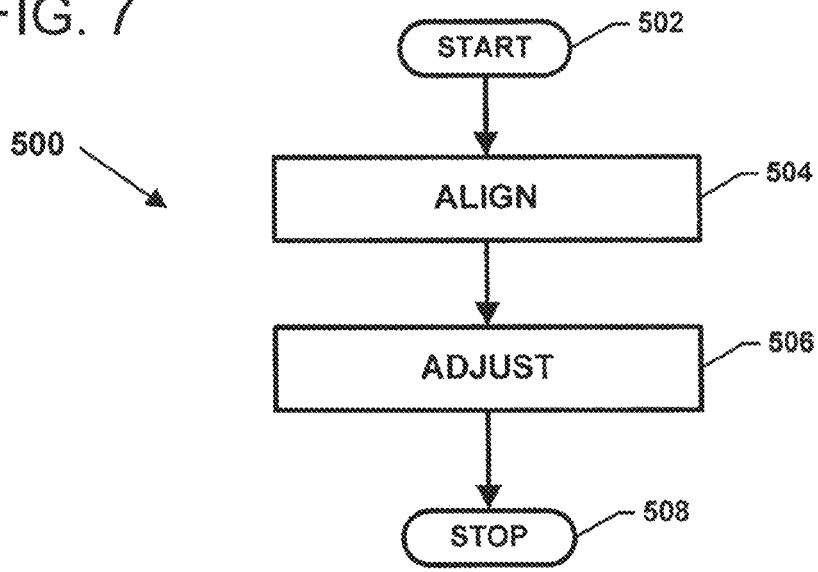
FIG. 7 is a flowchart illustrating an example align process by which a dental model can be associated with a 3D medical scan surface mesh in accordance with the principles of the present disclosure.

FIG. 7 is a flowchart illustrating an example align process 500 by which one or more dental model record can be matched with one or more 3D medical scan records in accordance with the principles of the present disclosure. The align process 500 is one example process for implementing the match operation 1008 of FIG. 1. The align process 500 initializes and begins at a start module 502 and proceeds to a position operation 504. In general, the position operation 504 determines an initial alignment for the dental model mesh or meshes with respect to the 3D medical scan mesh or meshes.

In some embodiments, the position operation 504 determines one or more common points or common areas represented by the polygonal meshes representing each data set. The position operation 504 also can determine which point or points in each polygonal mesh correspond to the common area(s). In some embodiments, the position operation 504 identifies an area on a second polygonal mesh, which is generated from the 3D medical scan record, that also is represented by a first polygonal mesh of the electronic dental model. The position operation 504 superimposes the electronic dental model mesh over the 3D medical scan record mesh at the general region of the identified common area.

In some embodiments, the position operation 504 facilitates interactive alignment of the dental model mesh relative to the 3D medical scan mesh by an operator. In one embodiment, the position operation 504 can facilitate interactive positioning using a drag and drop interface. For example, the user can translate and/or orient the first polygonal mesh with respect to the second polygonal mesh along six degrees of freedom.

In other embodiments, the position operation 504 can enable the operator to select one or more landmarks common between the two polygonal meshes. The dental model polygonal mesh is then superpositioned over the 3D medical scan polygonal mesh by manually or automatically aligning the common landmarks. In one embodiment, the operator selects points common between the meshes. In another embodiment, the operator selects polygons (e.g., triangles of the polygonal mesh) common between the two meshes. In yet another embodiment, the operator selects common areas represented by portions of polygons of the two meshes.

In one embodiment, automatic positioning of the dental model mesh can be performed by determining a first centroid representing the common region of the dental model mesh and a second centroid representing the common region of the 3D medical scan mesh. The position operation 504 transitions the dental model mesh over the 3D medical scan mesh based on the first and second centroids. In another embodiment, the selected corresponding landmarks can be fit together using standard point cloud registration techniques.

In certain embodiments, the position operation 504 can align three or more mesh models. For example, in one embodiment, the position operation 504 can match a first dental model mesh (e.g., representing a maxillary dentition) to a first 3D medical scan mesh (e.g., representing bone structure, gingival tissue, and/or nerve tissue of the maxilla). The position operation 504 also can match a second dental model mesh (e.g., representing a mandibular dentition) to a second 3D medical scan mesh (e.g., representing the bone structure, gingival tissue, and/or nerve tissue of the maxilla). In such cases, the position operation 504 can superimpose the maxillary dentition at an appropriate position over the maxilla shown in the 3D medical scan record and superimposes the mandibular dentition at an appropriate position over the mandible shown in the 3D medical scan record.

An adjust operation 506 fine tunes the alignment of the dental model mesh or meshes with the 3D medical scan mesh or meshes. In one embodiment, to provide improved matching, the adjust operation 506 conducts a matching process using a best-fit alignment algorithm. The align process 500 completes and ends at a stop module 508.

One example of a suitable best-fit alignment algorithm is an iterative, closest-point algorithm. Such a best-fit alignment algorithm tends to provide more accurate identification of the data points representing common surfaces between the data sets. The iterative, closest-point algorithm is an iterative alignment algorithm that works in three phases: 1) establish correspondence between pairs of features in the two structures that are to be aligned based on proximity, 2) estimate the rigid transformation that best maps the first member of the pair onto the second and then 3) apply that transformation to all features in the first structure. These three steps are then reapplied until convergence is concluded. Although simple, the algorithm works quite effectively when given a good initial estimate (e.g., when the dental model is superimposed in the general region of the common area of the 3D medical record).

More precisely, such a point matching algorithm is represented by:

Let S be a set of $N_S$ points $\{s_1, \ldots, s_{N_S}\}$ and M be the model. Let $\|\vec{s} - \vec{m}\|$ be the Euclidean distance between point $\vec{s} \in S$ and $\vec{m} \in M$. Let $CP(\vec{s}, M)$ be the closest point in M to the scene point $\vec{s}$.

1. Let $T^{[0]}$ be an initial estimate of the rigid transformation.
2. Repeat for k=1 ... $k_{max}$ or until convergence:
   1. Compute the set of correspondences $C = U_{i=1}^{Ns}\{(\vec{s}_i, CP(T^{[k-1]}(\vec{s}_i), M))\}.$ 2. Compute the new Euclidean transformation $T^{[k]}$ that minimizes the mean square error between point pairs in C.

The basic algorithm has been previously extended in a number of ways: 1) correspondence between a point and a tangent plane to overcome the lack of an exact correspondence between the two sets, 2) robustifying the algorithm to the influence of outliers and features lacking correspondences, 3) using a weighted least-square error metric, and 4) matching between features using a metric trading off distance and feature similarity (based local shape invariances). All of these approaches assume a rigid Euclidean transformation between the corresponding features, whereas the method presented here uses projective correspondence.

This projective correspondence process can be known as "wiggling" and is believed to provide a more accurate alignment between the data sets or images. The application of the closest-point algorithm to sections of the dental model (e.g., a maxillary section and a mandibular section) provides a best fit with the corresponding sections between the dental models and the 3D medical scan record. It has been found that application of the best-fit alignment algorithm to separate sections of the dental model provides a more accurate alignment and removes possible problems introduced by matching the entire dental model wherein the mandibular and maxillary dentitions are positioned in a different relative arrangement from the mandible and maxilla in the 3D medical scan record. The best-fit alignment algorithm is applied iteratively and it has been found that application of between 5 and 10 iterations provides satisfactory results.

d. Combining the Two Electronic Records

Each of the polygonal meshes includes data points that can represent overlapping regions (e.g., each of the data records can include points representing the teeth of the patient). In general, combining the data set includes removing duplicative data points so that the combined data set will cleanly and accurately reflect the scanned region. In one embodiment, the combined data set includes the more accurate of the data points from the data sets for each common area. For example, the combined data set can include data points from a dental model mesh that represent the teeth of the patient and data points from a 3D medical scan mesh that represent the condyles of the patient. In one embodiment, the combined polygonal mesh also can include data points from a second CT scan mesh that represent the roots of the teeth.

Figure 8:
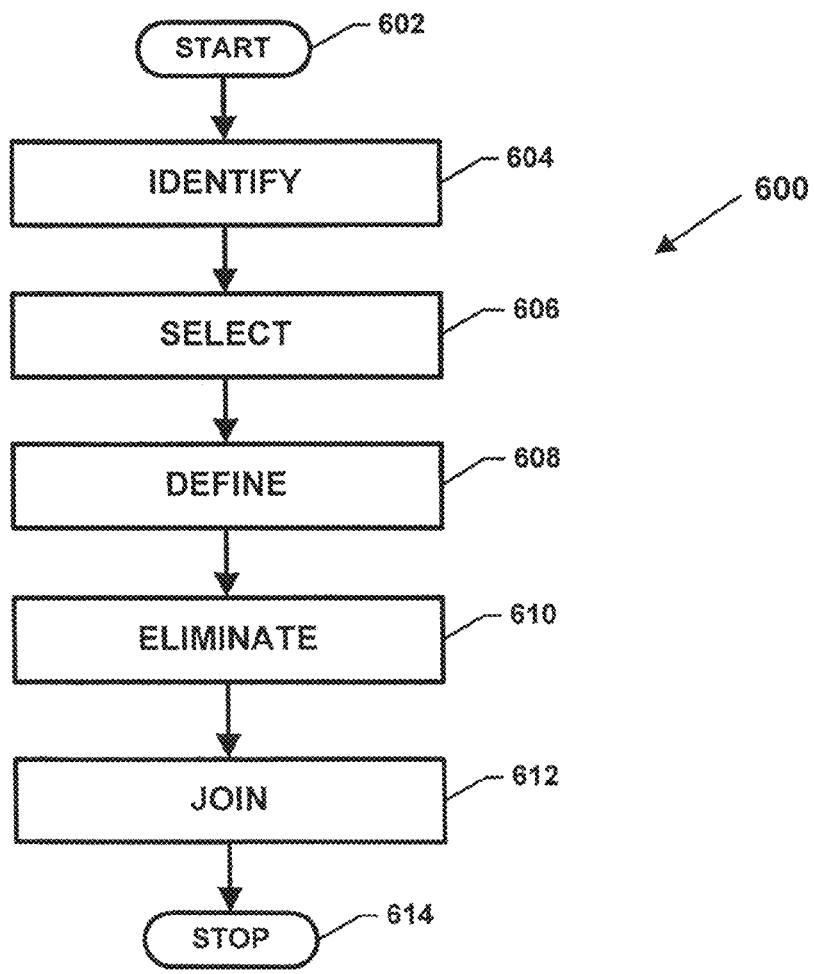
FIG. 8 is a flowchart illustrating an example merge process by which a dental model record can be integrated with a 3D medical scan record in accordance with the principles of the present disclosure.

FIG. 8 is a flowchart illustrating an example merge process 600 by which a first dental model polygonal mesh can be integrated with a second 3D medical scan polygonal mesh in accordance with the principles of the present disclosure. For ease in understanding, the merge process 600 will be disclosed in terms of merging one dental model mesh with one 3D medical scan mesh. In other embodiments, however, one or more dental model meshes can be merged with surface meshes of one or more 3D medical scan records using the merge process 600. The merge process 600 is one example process for implementing the combine operation 1010 of FIG. 1.

The merge process 600 initializes and begins at a start module 602 and proceeds to an identify operation 604. The identify operation 604 identifies a common (i.e., overlapping) region between the polygonal meshes. In certain embodiments, the identify operation 604 selects one of the common areas identified by the alignment process 500 of FIG. 7. For example, in one embodiment, the identify operation 604 selects a mandibular region that is represented in both the mandibular surface mesh of the 3D medical scan record and the mandibular dentition portion of the dental model mesh. In another embodiment, the identify operation 604 can select an individual tooth represented in both the 3D medical scan mesh and the dental model mesh.

A select operation 606 selects a master data set for the common area based on which of the polygonal meshes provides more accurate positional information for the common area selected in the identify operation 604. The unselected data set becomes the secondary data set for that area. In one embodiment, the select operation 606 selects the dental model mesh as the master data set when the identify operation 604 selects the occlusal surface of one or more teeth as the common area. In another embodiment, the select operation 606 selects the 3D medical scan surface mesh as the master data set when soft tissue surrounding the teeth is selected as the common area.

A define operation 608 identifies a set of data points and associated polygons within the secondary data set that correspond to the identified common area. In certain embodiments, the define operation 608 identifies the data points by defining an elimination volume around the common area. In one example embodiment, the define operation 608 can identify any data points representing the virtual space occupied by a dental model mesh of a maxillary arch, a dental model mesh of a mandibular arch, and any space located therebetween when the dental model meshes are positioned relative to each other.

In some embodiments, the define operation 608 identifies data points contained within the elimination volume. In other embodiments, the define operation 608 identifies polygons of the secondary mesh that are contained at least partially within the elimination volume (i.e., that are defined by at least one point residing within the elimination volume). In such embodiments, the define operation 608 also can identify points defining the identified polygon, even if those points do not actually fall within the elimination volume themselves. In still other embodiments, the define operation 608 identifies only polygons contained entirely within the elimination volume.

An eliminate operation 610 deletes the identified data points from the secondary data set. In one embodiment, the eliminate operation 610 produces a new data set including all data points from the secondary data set except the data points identified in define operation 608. A join operation 612 replaces the data points removed by the eliminate operation 610 with the data points of the master data set that represent the identified common area. In one embodiment, the join operation 612 inserts the appropriate data points from the master data set into the new data set produced in the eliminate operation 610. In another embodiment, the join operation 612 inserts the appropriate data points from the master data set into the secondary data set.

The merge process 600 completes and ends at a stop module 614.

e. Example Applications

Referring to FIGS. 9-18, the principles of the present disclosure can be best understood by walking through some example applications of the disclosed processes. FIGS. 9-12 illustrate a first example application in which a dental model image is integrated with a 3D medical scan image, for example, using the example integration process 1000 disclosed in FIG. 1. The integration process 1000 initializes and begins at a start module 1002 and proceeds to a first obtain operation 1004.

Figure 9:
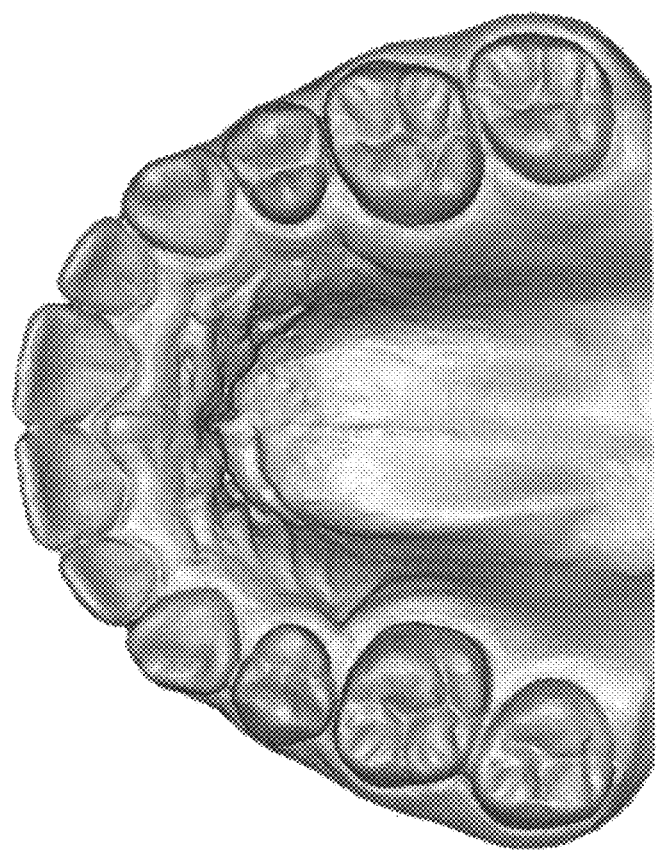
FIGS. 9-18 illustrate example applications in which one or more dental model images are integrated with a 3D medical scan image in accordance with the principles of the present disclosure.

The first obtain operation 1004 of the integration process 1000 acquires a first set of scanned data. In the example shown in FIG. 9, the first set of scanned data includes a maxillary dentition including teeth and surrounding gingival tissue of a person. In one embodiment, the first obtain operation 1004 scans a casting of the maxillary dentition using a laser line scanner. A dental model polygonal mesh of the maxillary dentition can be generated based on the scanned data as shown in FIG. 9. In one embodiment, the dental model mesh can be displayed at any orientation. For example, FIG. 9 shows a bottom, plan view of the dental model mesh. In another embodiment, the orientation of the displayed dental model mesh can be adjusted freely by a user.

Figure 10:
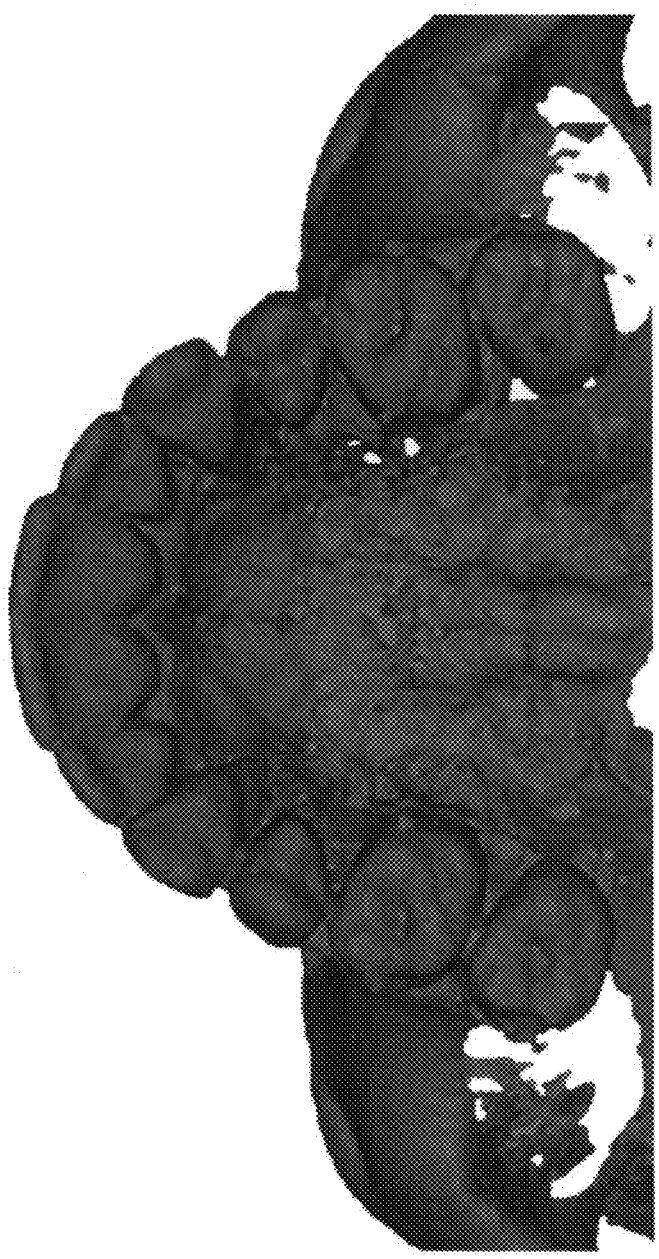
Figure 11:
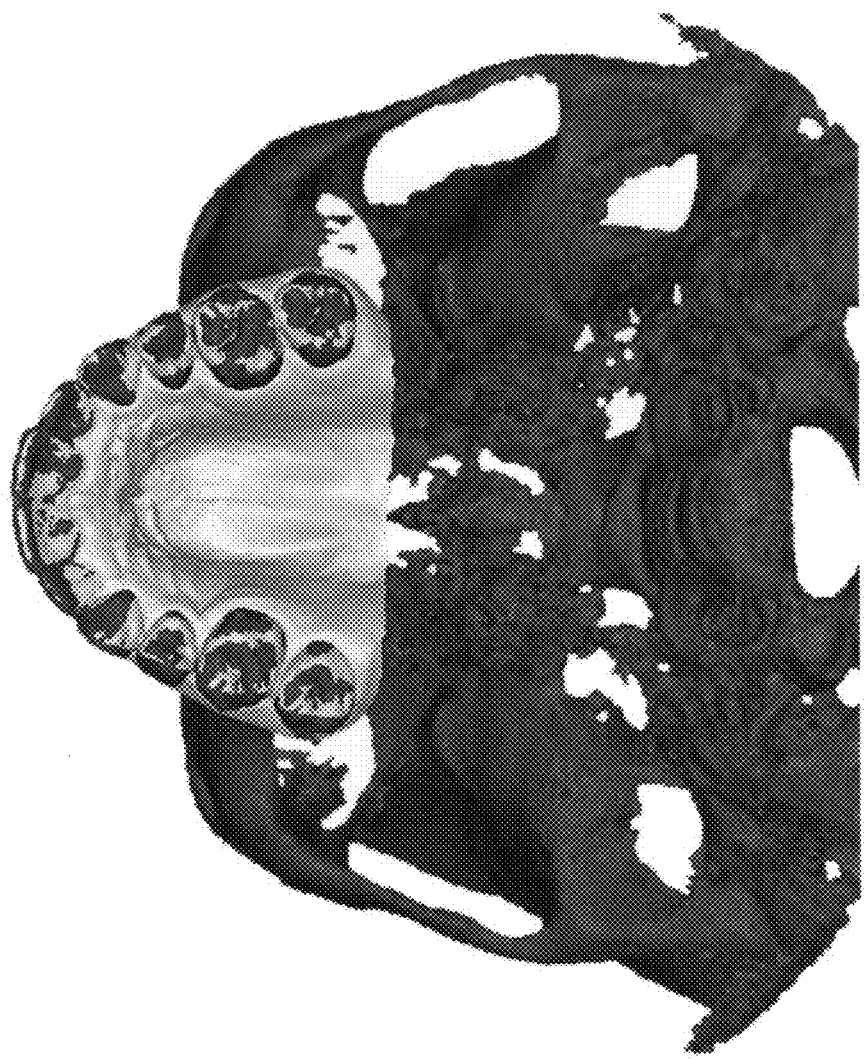
Figure 12:
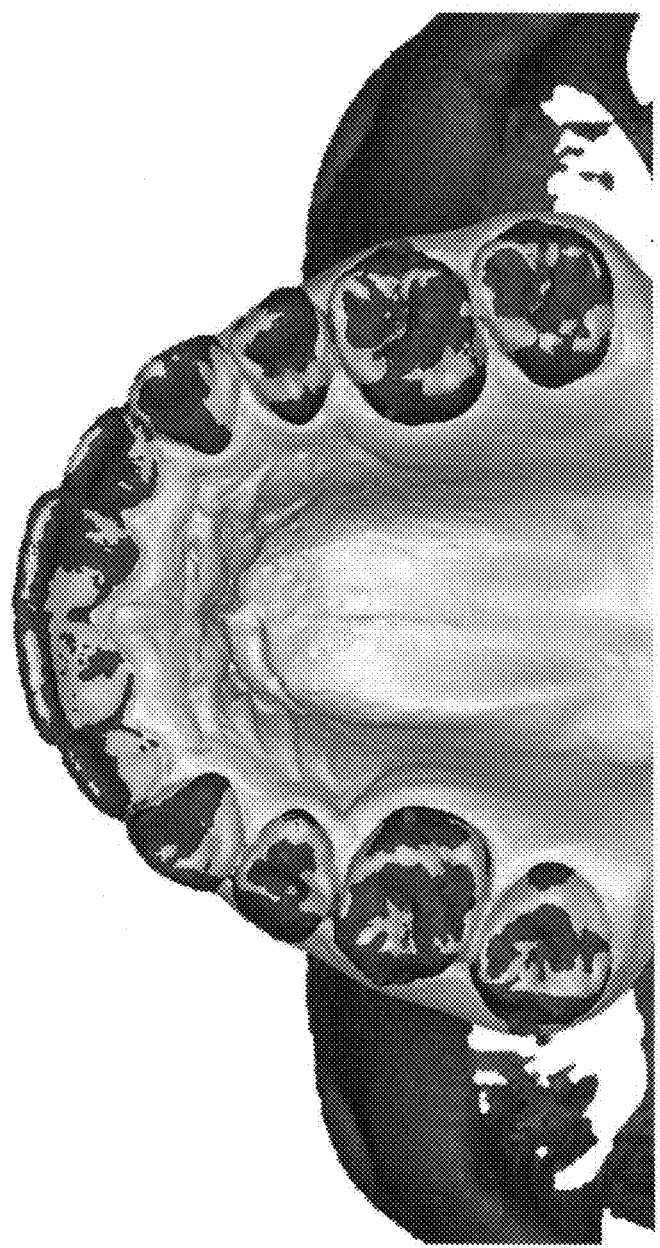
Figure 13:
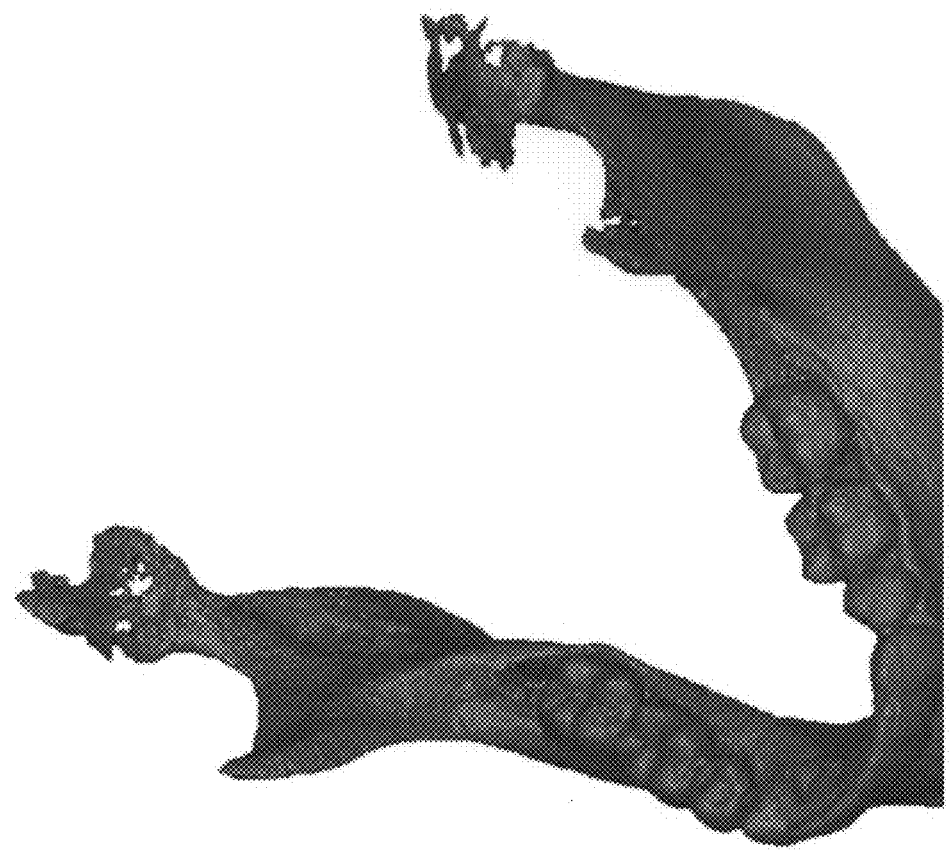
Figure 14:
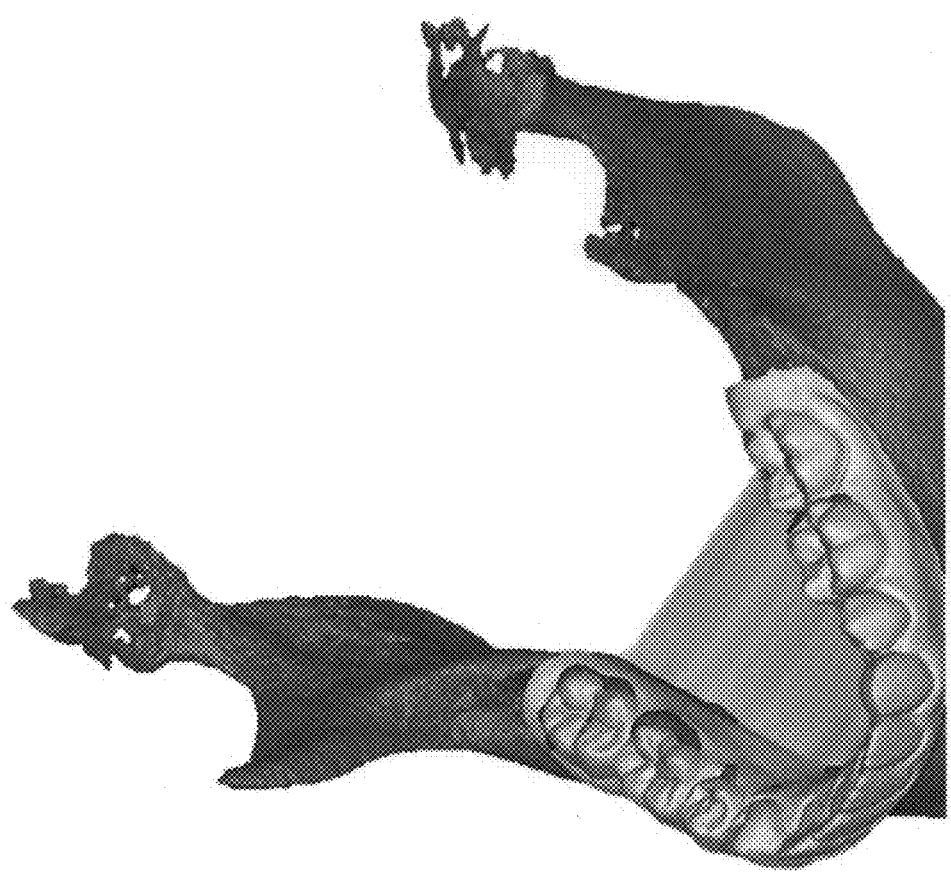
Figure 15:
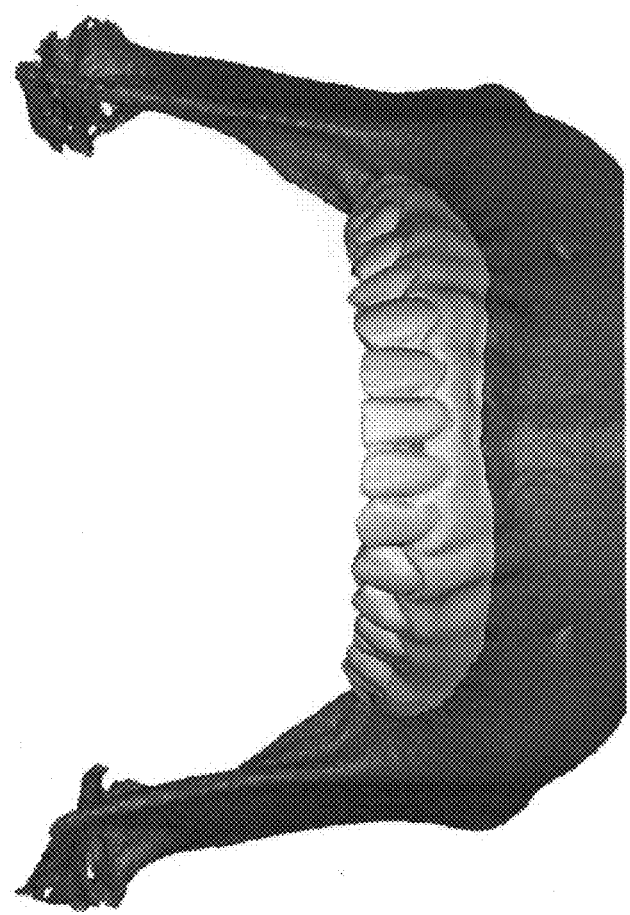

The second obtain operation 1006 of the integration process 1000 acquires a second set of scanned data. In the example shown in FIG. 10, the second set of scanned data includes a maxilla of a patient including the teeth, surrounding soft tissue, and surrounding bone structure. In one embodiment, the second obtain operation 1006 scans the cranio-facial region of the person using a CT scanner. A surface mesh representing the scanned area can be generated based on the scanned data points as shown in FIG. 10. In one embodiment, the surface mesh can be displayed at any orientation. For example, FIG. 10 shows a bottom, plan view of the surface mesh. In another embodiment, the orientation of the displayed surface mesh can be adjusted freely by a user.

The match operation 1008 determines the relationship between the first and second sets of data by determining which points in the first and second data sets represent common areas. For example, in one embodiment, the match operation 1008 determines which portions of the dental model and the surface mesh correspond to the occusal surfaces of the anterior teeth, which portions correspond to the occlusal surfaces of the posterior teeth, and/or which portions correspond with the palate surface. The match operation 1008 also can position the dental model relative to the surface mesh so as to generally align the dental model mesh and the surface mesh. In one embodiment, the match operation 1008 also fine tunes the alignment of the dental model mesh and the surface mesh.

The combine operation 1010 merges the dental model with the surface mesh to produce a combined image of the maxillary region of the person. In the example shown in FIGS. 11 and 12, the combine operation 1010 determines which sections of the dental model mesh are more accurate than the 3D medical scan surface mesh. The combine operation 1010 replaces the less accurate portions of the 3D medical scan surface mesh with the more accurate portions of the dental model mesh. Alternatively, the less accurate portions of the dental model mesh can be replaced by the more accurate portions of the 3D medical scan surface mesh.

The resulting combined image can be viewed and optionally manipulated by the user. For example, the user can adjust the orientation of the combined image to view the combined image from any perspective. The user also can adjust the scope of the combined image. For example, FIG. 12 includes a portion of the combined image of FIG. 11. The oral surgeon now has a more accurate medical file of the patient's craniofacial anatomy and dental structure from which to plan the potential surgery process.

Advantageously, the accuracy of the data set on which the combined image is based is enhanced by including the more accurate data of the two data sets for each common area. In addition, when viewing the combined image, feature represented in only one of the data sets can be viewed concurrently with features represented in only the other of the data sets.

Other example embodiments are shown with respect to FIGS. 13-18. In the example shown in FIG. 14, the first set of scanned data includes a mandibular dentition including teeth and the surrounding gingival tissue of a person and the second set of scanned data includes a mandible of a patient including the teeth, surrounding soft tissue, and surrounding bone structure (also see FIG. 13). The first and second data sets are shown matched and combined in FIGS. 14 and 15.

Figure 16:
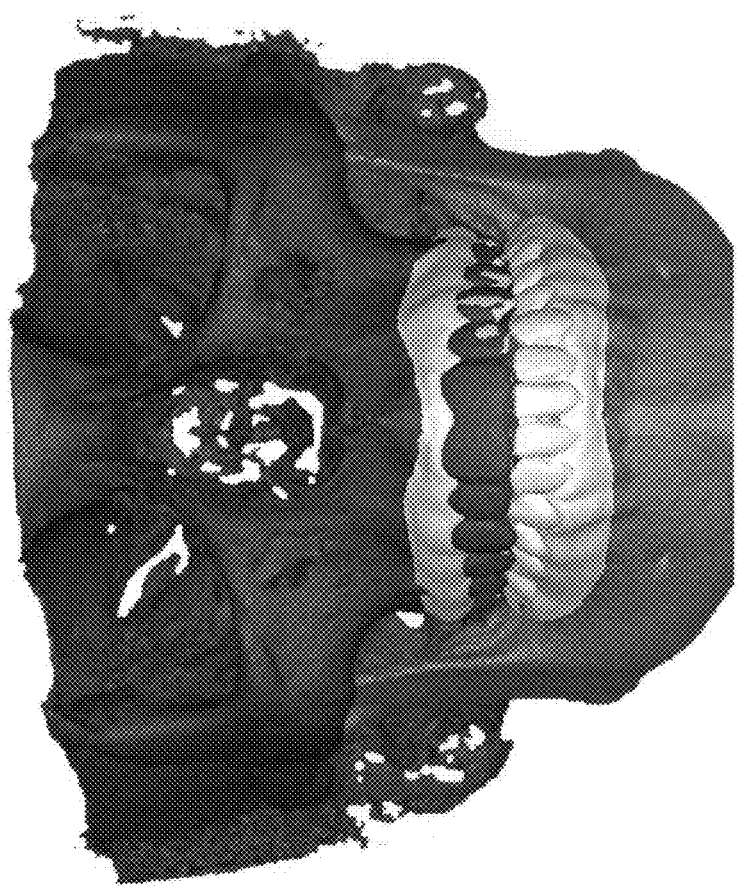
Figure 17:
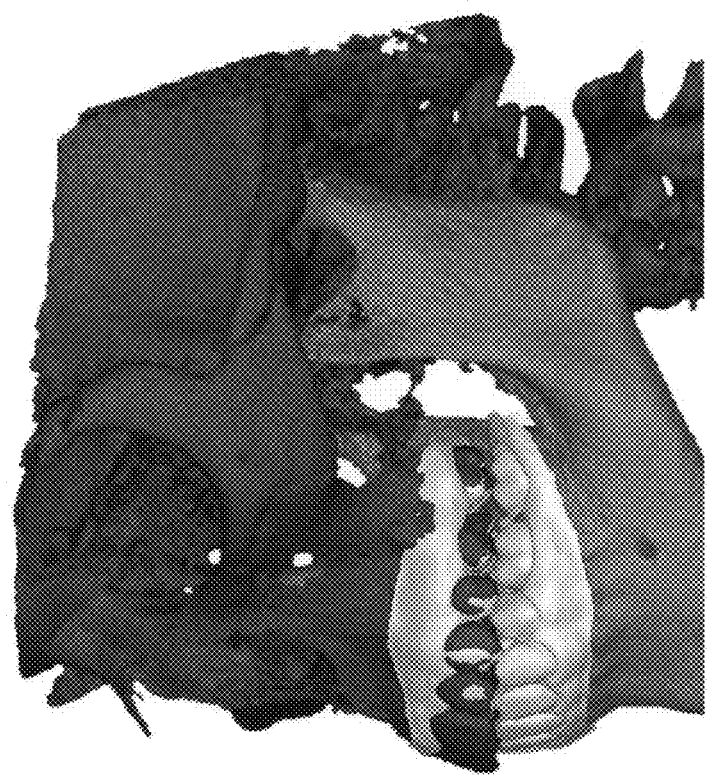
Figure 18:
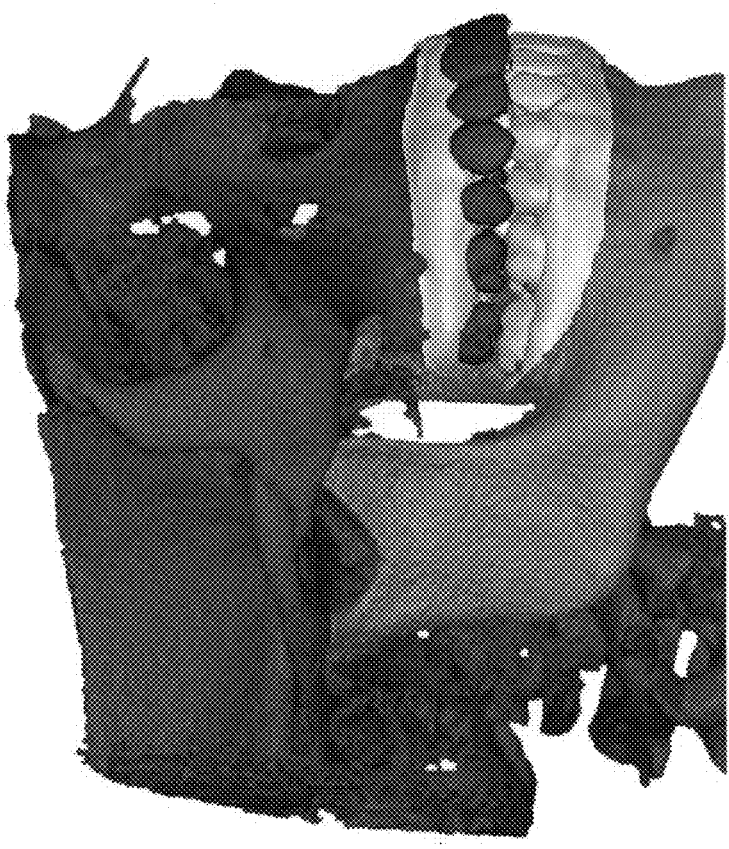

FIGS. 16-18 illustrate a combined image of a first dental model of a mandible and a second dental model of a maxilla integrated with a 3D medical scan of the skull of a person. In the example shown, the first dental model of the mandibular arch is determined to be more accurate than the 3D medical scan surface mesh of the mandible of the person. Accordingly, the mandible portion of the 3D medical scan surface mesh has been replaced by the first dental model. Only portions of the second dental model of the maxillary arch, however, have been identified as more accurate than the 3D medical scan surface mesh of the maxilla. Accordingly, only portions of the maxilla portion of the 3D medical scan surface mesh (e.g., the gingival tissue surrounding the teeth) has been replaced with the second dental model.

f. Treatment Planning

The integration of the accurate dental model meshes of a patient's dentition with nerves, joints, and other patient oral anatomy information provided in the 3D medical scans can provide an examining medical professional with a more comprehensive record of the patient's oral anatomy. Accordingly, the medical professional can determine an appropriate course of treatment with the aid of supporting software tools for simulating surgical procedures on the computer. For example, in some embodiments, the medical profession can determine where to drill or cut during surgery based on the patient's bone structure and arrangement of soft tissue.

In other embodiments, the medical profession can determine which orthodontic treatments will cause nerves and/or roots of the teeth to touch or otherwise violate predetermined placement constraints. Examples of positioning constraints include preferences for roots to be arranged to avoid pressing against each other. Another example of positioning constraints is a preference for avoiding placing roots within or adjacent sinuses (i.e., or other voids) to ensure adequate anchorage is provided for the roots. Another example positioning constraint is a preference for a root to be arranged generally parallel or co-linear with an axis of the corresponding tooth.

In one embodiment, alerts can be displayed to indicate when a planned course or treatment will violate one or more positioning constraints. For example, a dialog box can be displayed indicating that a positioning constraint is being violated. Such a dialog box also can indicate changes to the treatment that would mitigate or alleviate the violation. In another embodiment, color mapping can be utilized with the dental model mesh and/or with the 3D medical scan mesh to indicate when treatments violate the positioning constraints. For example, in one embodiment, a root violating the positioning constraint can be colored red or another attention-grabbing color. In another embodiment, different colors can be mapped over the mesh surface of the roots, teeth, or other sections of the images to indicate distances between different portions of the images (e.g., where each color represents a different distance).

In other embodiments, a location of a condyle can be identified based on the combined polygonal mesh of the dental model record and the 3D medical scan record. Also, range-of-motion constraints of the condyle can be identified based on either the 3D scan record polygonal mesh or the combined polygonal mesh. Motion of the condyle can be observed and studied/analyzed by driving a digital articulator based on the identified condyle location and range-of-motion constraints. Such observation also can aid in treatment planning.

g. Scaling and Calibration

In general, measurements of anatomical features of a patient can be obtained from the dental model mesh. For example, the dental model mesh can be used to measure the width of a patient's soft palate or a height of a cusp on a particular tooth.

Typically, a 3D medical scan or surface mesh thereof cannot be used to obtain measurements of anatomical features. The 3D medical scanner can obtain an inaccurate positional due to distortions or operating malfunctions. For example, the scale of the obtained positional data can differ from the scale of the anatomical features being scanned.

In certain embodiments, a scaling factor can be applied to the dental model mesh to properly align the dental model mesh with the 3D medical scan mesh. For example, an operator can determine a scaling factor that, when applied to the dental model, causes an arch width obtained from the dental model mesh to match an arch width obtained from the 3D medical scan mesh.

The transformation factor by which the 3D medical scan deviates from the object being scanned can be determined based on this scaling factor. Accordingly, the dental model mesh can facilitate calibration of the 3D medical scanner. For example, in one embodiment, comparison of the dental model mesh and the 3D medical scan surface mesh can indicate that the 3D medical scanner is off by a given scaling factor. In other embodiments, the 3D medical scanner can be calibrated by scanning one or more artifacts having known dimensions.

h. Combining 3D Surface Meshes with 2D Images

In certain embodiments, two-dimensional (2D) and/or three-dimensional (3D) images, such as digital photographs, can be mapped onto the surfaces of the 3D dental model mesh and/or the 3D medical scan surface mesh. Such texture mapping enhances the photo-realism of the mapped surface. In addition, by mapping features from 2D images onto more accurate 3D images, the accuracy of measurements between features included in the 2D images can be enhanced.

In general, a 2D image is mapped to the 3D image by matching landmarks identified in each data set. In some embodiments, landmarks of the 2D image can be mapped to landmarks the 3D image using the matching and merge processes described above. After mapping the landmarks, the remaining data points from the 2D image can be copied and/or interpolated onto the 3D data set. In one embodiment, the mapped data points of the 2D image replace the corresponding data points from the 3D data set.

One example of mapping a 2D data set onto a 3D data set includes the mapping of Cephalometric Radiographs and/or tracings onto the dental model record. In general, a 2D Cephalometric Radiograph can be converted into a polygonal mesh that can be transformed (e.g., translated, resized, rotated, etc.) and/or deformed (e.g., stretched, wrapped, twisted, etc.) to match corresponding anatomical features on the dental model record. For example, a 2D image can be converted to a triangular polygonal mesh by assigning a color obtained from each pixel of the 2D image to two triangles of the polygonal mesh forming a square. Panoramic X-ray images can be converted and transformed in the same manner.

By mapping the Cephalometric Radiograph to the dental model record, root tip information can be displayed to the user in a more intuitive manner. For example, the clinical roots represented by the Cephalometric Radiograph can be shown extending outwardly from the clinical crowns represented by the dental model record. Such mapping also can enhance the accuracy of root placement relative to the teeth in comparison to a 2D panoramic radiograph taken of the patient.

In certain embodiments, one or more 2D color photographs of teeth of a patient can be wrapped over all or part of an exterior of the 3D dental model record. In another embodiment, one or more digitized pictures of the face (e.g., showing the skin, eyes, nose, lips, and/or other soft tissue) of a patient obtained with a 3D camera can be mapped onto all or part of an exterior of the 3D medical scan record. In one embodiment, texture mapping enables a technician to view the soft tissue of the lips represented by a color photograph laid over the skeletal structure of a patient represented by a 3D medical scan record and/or over the teeth represented by the dental model record.

Texture mapping also can provide additional information to the user to aid in developing a surgical plan, an orthodontic plan, a dental plan, or other course of action. For example, texture mapping can enable a technician to better understand how modification to the skeletal structure or to the dentition of the patient will affect the soft tissue and/or outward appearance of the patient. In one embodiment, such soft tissue deformation can be determined based on the thickness and durometer of the soft tissue and the intensity and direction of the force being applied to the soft tissue (e.g., by a tooth being shifted towards the soft tissue). Soft tissue deformation also can be determined based on finite element analysis of a particular type of types of soft tissue being deformed.

i. Customized Appliances, Splints, and Other Dental, Orthodontic, and/or Surgical Structures The integration of the polygonal meshes of the maxillary and mandibular occlusal surfaces of the dental model record (e.g., showing the occlusal surfaces in a closed bite position) with the 3D medical scan record of a patient's oral anatomy can provide the examining medical professional with a more comprehensive record of the patient's oral anatomy. Accordingly, with supporting software tools for simulating surgical procedures on the computer, such a medical professional can design and optionally produce customized versions of restorative appliances (e.g., a dental crown, a dental bridge, or a dental implant), orthodontic appliances (e.g., brackets, placement trays, etc.), and/or surgical splits. For example, a medical professional can create any of the following splints used in the treatment of orthotic, orthognathic, and restorative dental problems requiring surgical correction: (1) orthotic splint for alleviating temporomandibular joint (TMJ) dysfunction; (2) orthognathic surgical splint for configuring a patient's dentition into final occlusion during and/or after surgery; and/or (3) dental implant surgical splint for establishing surgical drill alignment in a sterilizeable (e.g., plastic) splint that is specifically fit to the patient's existing teeth.

Figure 19:
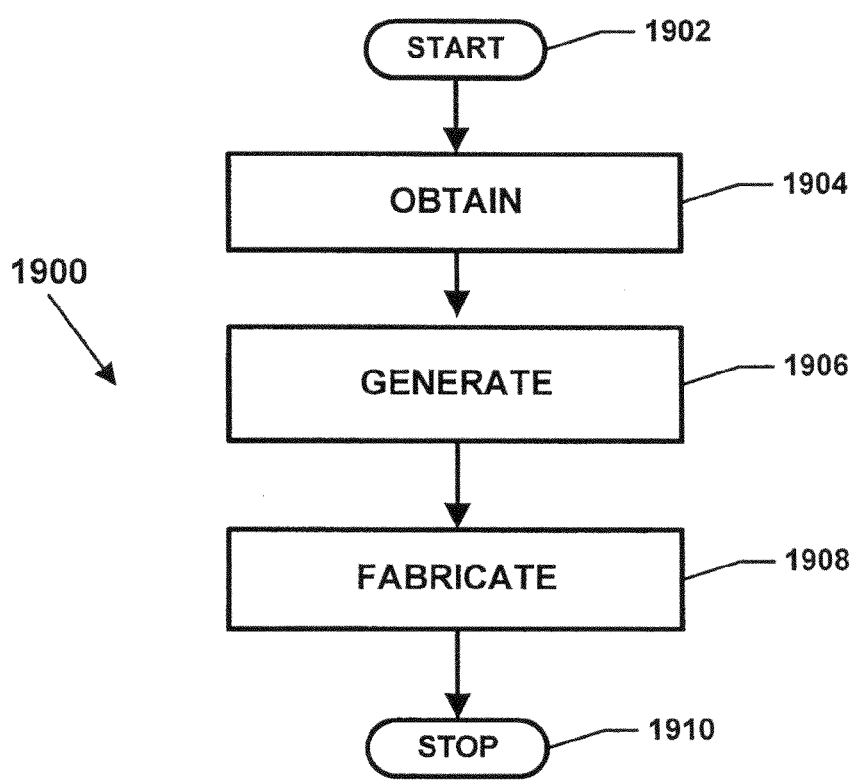
FIG. 19 is a flowchart illustrating an operational flow for an example creation process by which a surgical apparatus, such as a surgical splint, can be designed and fabricated in accordance with the principles of the present disclosure.

FIG. 19 is a flowchart illustrating an operational flow for a creation process 1900 for creating a customized dental, orthodontic, or surgical structure in accordance with the principles of the present disclosure. For example, the creation process 1900 can be used to design and fabricate a customized dental appliance configured to mount to a preparation site on the patient's dentition. The creation process 1900 also can be used to design and fabricate a customized splint configured to mount to a preparation site on the skeletal structure of the patient. The creation process 1900 initializes and begins at a start module 1902 and proceeds to an obtain operation 1904.

The obtain operation 1904 acquires or otherwise receives positional data indicating the location and/or dimensions of the preparation site at which the customized structure is to be mounted. In one embodiment, the obtain operation 1904 acquires positional data representing a portion of the dentition of the patient. An example of such positional data includes the data set from the dental model record described above. In another embodiment, the obtain operation 1904 acquires positional data representing a portion of the skeletal structure of the patient's mandible and/or maxilla. An example of such positional data includes the data set from the 3D medical scan record described above. In other embodiments, the positional data also can indicate positions of adjacent teeth, antagonistic teeth, soft tissue, and/or skeletal anatomical features relative to the preparation site.

A generate operation 1906 creates an electronic model (e.g., a polygonal, surface mesh model) of the customized structure based on the obtained positional data representing the preparation site. In general, the generate operation 1906 produces an electronic model of a customized structure that is shaped and dimensioned to enable the customized structure to mount to the preparation site. The customized structure can be produced by transferring positional data of the generated electronic model to any commercially available fabrication device, such as a Rapid Prototyping Device.

A fabricate operation 1908 produces at a fabrication device a physical customized structure in accordance with the electronic model created in the generate operation 1906. In one embodiment, the fabricate operation 1908 prints or mills the customized structure directly from a biocompatible material based on the positional data of the generated electronic model. In another embodiment, the fabricate operation 1908 prints or otherwise forms a pattern of the customized structure and then produces the physical customized structure from the pattern. For example, the fabricate operation 1908 can rapid prototype a wax pattern of the customized structure and cast the customized structure using lost-wax casting. One example of a rapid prototyping machine used to print wax models is the Patternmaster wax printer from Solidscape of Connecticut. However, any type of rapid prototyping process can be used without deviating from the spirit and scope of the disclosure. The creation process 1900 completes and ends at a stop module 1910.

While a particular embodiment of the invention has been described, it will be understood that by those skilled in the art that the invention is not limited by the application, embodiment or the particular devices disclosed and described herein. It will be appreciated that other devices that embody the principles of this invention and other applications therefor other than as described herein can be configured within the spirit and intent of this invention. The system described herein is provided as only one example of an embodiment that incorporates and practices the principles of this invention. Other modifications and alterations are well within the knowledge of those skilled in the art and are to be included within the broad scope of the appended claims.

It can be appreciated that cone beam computer tomography and digitizing of a plaster cast through precision digital scanning eliminates measurement differences and inaccuracies due to imprecision with location of the measuring devices.

It can further be appreciated that inaccuracies due to difficulties in superimposing a dental model of a scanned region onto a 3D medical scan record including the same scanned region are compensated with a best match process being applied to one or more sections of the dental model. Inaccuracies from consistently locating artificial landmarks also are eliminated with the present disclosure.

What is claimed is:

1. A method for creating a polygonal mesh of an anatomical region on a patient, the method comprising:
   obtaining a first polygonal mesh representing at least a portion of the anatomical region;
   obtaining a second polygonal mesh representing at least a portion of the anatomical region;
   positioning the first polygonal mesh at an appropriate location with respect to the second polygonal mesh;
   determining common regions between the polygonal meshes;
   selecting one of the polygonal meshes as a master polygonal mesh and another of the polygonal meshes as a secondary polygonal mesh for each common region;
   eliminating duplicative data in the secondary polygonal mesh for each common region; and
   joining together the master polygonal mesh for each region to produce a combined polygonal mesh representing the anatomical region of the patient.

2. The method of claim 1, wherein the first polygonal mesh is a dental model polygonal mesh and the second polygonal mesh is a 3D medical scan polygonal mesh.

3. The method of claim 2, further comprising:
   acquiring the dental model including a first data set of positional data representing the anatomical region of the patient; and
   generating the dental model polygonal mesh based on the acquired first data set.

4. The method of claim 2, further comprising:
   acquiring the 3D medical scan including a second data set of positional data representing the anatomical region of the patient;
   generating the 3D medical scan polygonal mesh based on the acquired second data set.

5. The method of claim 2, wherein positioning the dental model polygonal mesh comprises positioning the dental model polygonal mesh at a generally appropriate location relative to the 3D medical scan polygonal mesh using a rough match-up algorithm.

6. The method of claim 5, wherein positioning the dental model polygonal mesh further comprises refining the generally appropriate location to an appropriate location using a matching process.

7. The method of claim 6, wherein the matching process utilizes a best-fit algorithm.

8. The method of claim 1, wherein eliminating duplicative data comprises defining an elimination volume within the secondary polygonal mesh; and
   eliminating any data points contained within or associated with data points contained within the defined elimination volume.

9. The method of claim 7, wherein a data point is associated with the defined elimination volume if the data point partially defines a polygon of the secondary polygonal mesh that is contained within the elimination volume.

10. The method of claim 2, wherein the 3D medical scan polygonal mesh does not include positional data for any artificial fiducial structure common to the dental model polygonal mesh.

11. The method of claim 1, further comprising:
    identifying an installation site on the combined polygonal mesh;
    designing a customized structure configured to mount to the installation site on the combined polygonal mesh; and
    fabricating the customized structure.

12. The method of claim 11, wherein designing the customized structure comprises designing a surgical splint configured to mount to skeletal anatomy of the patient.

13. The method of claim 11, wherein designing the customized structure comprises designing a dental appliance configured to mount to at least one prepared tooth of the patient.

14. The method of claim 1, further comprising:
    planning a course of treatment to modify of at least a portion of the anatomical region of the patient represented by the combined polygonal mesh; and
    displaying results from the course of treatment.

15. The method of claim 4, wherein generating the 3D medical scan polygonal mesh based on the acquired second data set comprises converting positional data indicating voxel volume to positional data representing a surface polygonal mesh.

16. The method of claim 2, further comprising:
    identifying a location of a condyle based on the combined polygonal mesh;
    identifying range-of-motion constraints of the condyle; and
    driving a digital articulator based on the identified condyle location and range-of-motion constraints.

17. A system for integrating a dental model record with a 3D medical scan record, the system comprising:
    a computer having a processor and a memory storage configured to store a first data set of positional data representing a three-dimensional polygonal mesh electronic model of a dentition of a patient and a second data set of positional data representing a two-dimensional 3D medical scan of a cranio-facial structure of the patient;

the computer being configured to store and implement a rough match-up algorithm for positioning the polygonal mesh electronic model at a generally appropriate location, a matching process for refining the generally appropriate location to an appropriate location, and an elimination module for defining an elimination volume of the 3D medical scan, the elimination volume containing positional data points common to the first data set and the second data set.

18. The system of claim 17, further comprising a laser-line scanner for obtaining the first data set.

19. The system of claim 17, further comprising a cone-beam 3D medical scanner for obtaining the second data set.

20. A computer program product, comprising a computer usable medium having a computer readable program code embodied therein, said computer readable program code adapted to be executed to implement a method for integrating a dental model record with a 3D medical scan record, the method comprising:

providing a system, wherein the system comprises a computer processor, memory, and distinct software modules, and wherein the distinct software modules comprise first and second obtain modules, a rough match-up processing module, a matching module, and an elimination module;

obtaining a first data set of positional data representing a three-dimensional polygonal mesh electronic model of a dentition of a patient from the memory of the system using the first obtain module;

obtaining a second data set of positional data representing a two-dimensional 3D medical scan of a cranio-facial structure of the patient using the second obtain module;

implementing the rough match-up processing module to position the polygonal mesh electronic model at a generally appropriate location with respect to the 3D medical scan;

implementing the matching module to refine the generally appropriate location to an appropriate location; and implementing the elimination module to define an elimination volume of the 3D medical scan, the elimination volume containing positional data points common to the first data set and the second data set.

\* \* \* \* \*